US011123236B2

(12) United States Patent
Chaudhary et al.

(10) Patent No.: US 11,123,236 B2
(45) Date of Patent: Sep. 21, 2021

(54) ABSORBENT ASSEMBLIES AND ABSORBENT ARTICLES INCLUDING A HYDROPHOBICALLY MODIFIED POLYMER

(71) Applicant: Kimberly-Clark Worldwide, Inc., Neenah, WI (US)

(72) Inventors: Vinod Chaudhary, Alpharetta, GA (US); Sarah Hartman, Flint, MI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 16/758,513

(22) PCT Filed: Oct. 30, 2017

(86) PCT No.: PCT/US2017/059005
§ 371 (c)(1),
(2) Date: Apr. 23, 2020

(87) PCT Pub. No.: WO2019/088970
PCT Pub. Date: May 9, 2019

(65) Prior Publication Data
US 2020/0253792 A1  Aug. 13, 2020

(51) Int. Cl.
*A61F 13/15* (2006.01)
*A61F 13/513* (2006.01)
(Continued)

(52) U.S. Cl.
CPC ...... *A61F 13/513* (2013.01); *A61F 13/49009* (2013.01); *A61F 13/51113* (2013.01); *A61L 15/24* (2013.01); *A61L 15/48* (2013.01)

(58) Field of Classification Search
CPC .......... A61L 15/24; A61L 15/42; A61L 15/48; C08L 33/08; A61F 13/49009; A61F 13/51113; A61F 13/513
See application file for complete search history.

(56) References Cited

U.S. PATENT DOCUMENTS 4,753,230 A *  6/1988  Carus .................. A61F 13/00
                                                602/47
6,300,258 B1  10/2001  Stano et al.
(Continued)

FOREIGN PATENT DOCUMENTS

JP       10509896 A    9/1998
KR    20160086348 A    7/2016
(Continued)

OTHER PUBLICATIONS

Piculell et al., "Binding of surfactants to hydrophobically modified polymers", Advances in Colloid and Interface Science, 63 (1996) 1-21.

*Primary Examiner* — Bradley H Philips

(57) ABSTRACT

An absorbent article can include a bodyside liner, an outer cover, and an absorbent body disposed between the bodyside liner and the outer cover. The bodyside liner can be treated with a surfactant. A component of the absorbent article can be treated with a hydrophobically modified polymer. The hydrophobically modified polymer can be configured to interact with the surfactant upon wetting of the absorbent article when the surfactant and the hydrophobically modified polymer are in an aqueous solution to increase surface tension of the aqueous solution.

19 Claims, 12 Drawing Sheets

(51) Int. Cl.
*A61F 13/49* (2006.01)
*A61F 13/511* (2006.01)
*A61L 15/24* (2006.01)
*A61L 15/48* (2006.01)

(56) References Cited

U.S. PATENT DOCUMENTS

| | | | |
|---|---|---|---|
| 7,626,073 B2 | 12/2009 | Catalan | |
| 7,820,608 B2 | 10/2010 | Walters et al. | |
| 7,935,860 B2 | 5/2011 | Dodge, II et al. | |
| 10,589,134 B2* | 3/2020 | Hoffman | A61K 8/4946 |
| 2001/0037100 A1* | 11/2001 | Shanklin | A61Q 19/00 |
| | | | 604/358 |
| 2002/0069988 A1* | 6/2002 | Yahiaoui | A61F 13/51121 |
| | | | 162/123 |
| 2002/0128615 A1* | 9/2002 | Tyrrell | A61K 8/25 |
| | | | 604/364 |
| 2005/0075256 A1 | 4/2005 | Librizzi et al. | |
| 2005/0136242 A1* | 6/2005 | Yahiaoui | A61L 15/48 |
| | | | 428/317.9 |
| 2005/0210601 A1 | 9/2005 | Strang et al. | |
| 2007/0038192 A1 | 2/2007 | Bentz | |
| 2008/0000503 A1 | 1/2008 | Hammock | |
| 2009/0155325 A1* | 6/2009 | Wenzel | A61L 15/34 |
| | | | 424/402 |
| 2012/0157366 A1 | 6/2012 | Anim-Danso et al. | |
| 2014/0128295 A1 | 5/2014 | Wagles et al. | |
| 2020/0352991 A1* | 11/2020 | Modak | A61K 36/53 |

FOREIGN PATENT DOCUMENTS

| | | | | |
|---|---|---|---|---|
| WO | 9635731 | A1 | 11/1996 | |
| WO | 9711220 | A1 | 3/1997 | |
| WO | 16006130 | A1 | 1/2016 | |
| WO | WO-2016160006 | A1 * | 10/2016 | A01N 25/34 |

* cited by examiner

ABSORBENT ASSEMBLIES AND ABSORBENT ARTICLES INCLUDING A HYDROPHOBICALLY MODIFIED POLYMER

TECHNICAL FIELD

The present disclosure relates to absorbent assemblies and absorbent articles.

BACKGROUND OF THE DISCLOSURE

A primary function of personal care absorbent articles is to absorb and retain body exudates such as urine, fecal material, blood, and menses with additional desired attributes including low leakage of the exudates from the absorbent article and a dry feel to the wearer of the absorbent article. Absorbent articles are commonly made with nonwoven components that are hydrophobic in nature. To aid in the intake of body exudates into absorbent systems of the absorbent articles, hydrophobic components of the absorbent article, such as the bodyside liner, are often treated with a surfactant. Surfactants help reduce the surface tension of an aqueous solution, such as that provided by an insult of a body exudate, to provide for improved intake of the aqueous solution.

Although surface tension reduction helps improve the intake of the aqueous solution provided by an insult of a body exudate, it can also lead to an undesirable product attributes of re-wet (or "flowback") and/or leakage after the absorbent article has been insulted with a body exudate. As an example, surfactants that reduce the surface tension of the aqueous solution created by body exudates can lead to increased re-wet, where the aqueous solution of body exudate fluids flow from the absorbent assembly back towards the user's skin, due to the reduction in surface tension of the aqueous solution. Surfactants may also increase the likelihood for potential leakage of the aqueous solution of body exudates through microgaps in gaskets of the absorbent article.

Thus, there is a desire for improvements to absorbent assemblies and absorbent articles that allow for proper intake of aqueous solution of body exudates, yet reduce the likelihood of re-wet and potential leakage of such aqueous solutions from the absorbent assemblies and absorbent articles.

SUMMARY OF THE DISCLOSURE

In one embodiment, an absorbent article can include a bodyside liner, an outer cover, and an absorbent body that is disposed between the bodyside liner and the outer cover. The bodyside liner can be treated with a surfactant. A component of the absorbent article can be treated with a hydrophobically modified polymer. The hydrophobically modified polymer can be configured to interact with the surfactant upon wetting of the absorbent article when the surfactant and the hydrophobically modified polymer are in an aqueous solution to increase surface tension of the aqueous solution.

In another embodiment, an absorbent assembly for use in an absorbent article that includes a surfactant for reducing surface tension of an aqueous solution can include an absorbent body. The absorbent body can include absorbent material. The absorbent assembly can further include a component that can be treated with a hydrophobically modified polymer. The hydrophobically modified polymer can be configured to interact with the surfactant upon wetting of the absorbent assembly when the surfactant and the hydrophobically modified polymer are in an aqueous solution to increase surface tension of the aqueous solution.

BRIEF DESCRIPTION OF DRAWINGS

A full and enabling disclosure thereof, directed to one of ordinary skill in the art, is set forth more particularly in the remainder of the specification, which makes reference to the appended figures in which.

Figure 1:
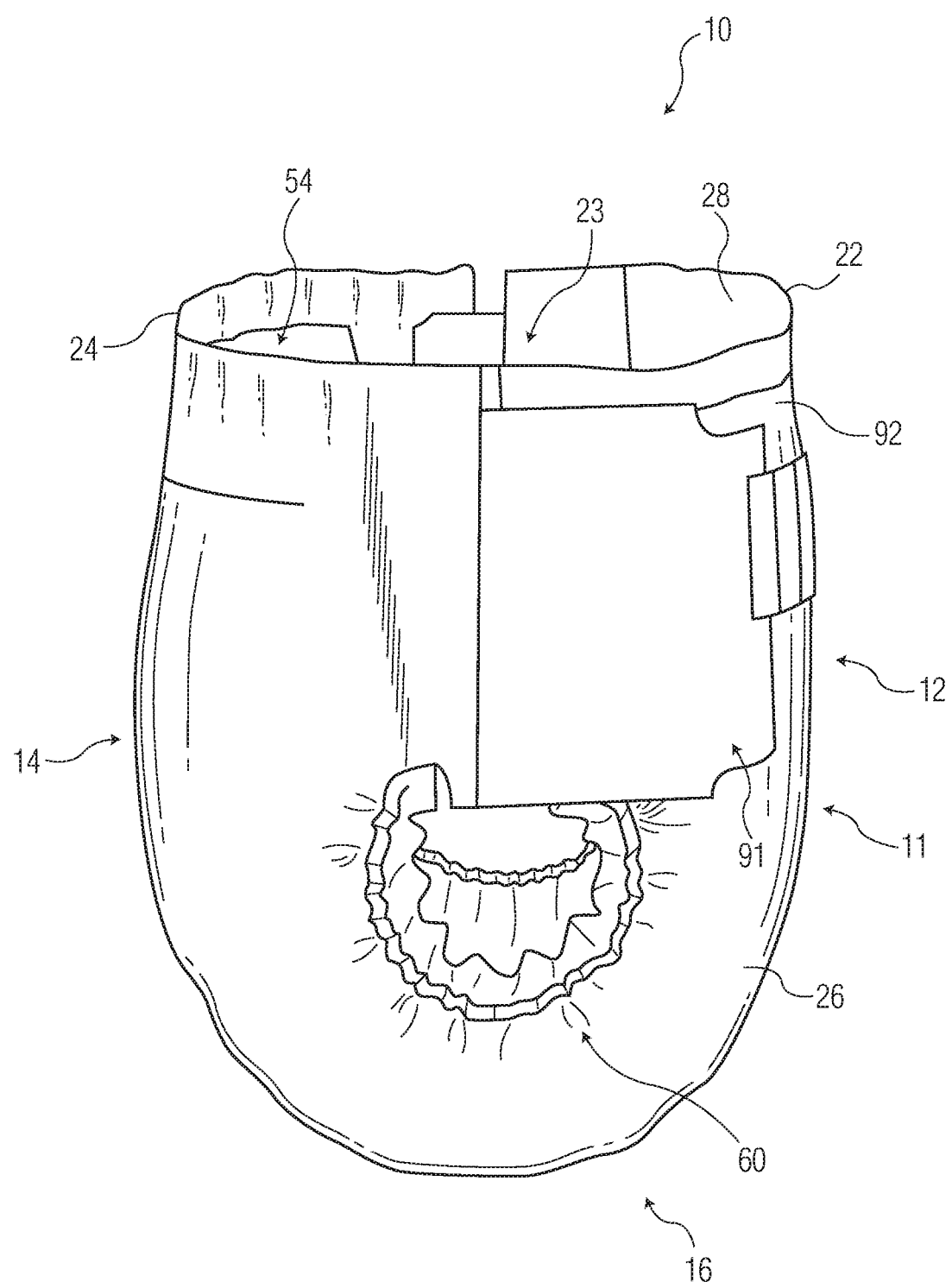
FIG. 1 is side perspective view of an exemplary embodiment of an absorbent article, such as a diaper, in a fastened condition.

Repeat use of reference characters in the present specification and drawings is intended to represent the same or analogous features or elements of the disclosure.

DETAILED DESCRIPTION OF THE DISCLOSURE

In an embodiment, the present disclosure is generally directed towards an absorbent article 10 and/or an absorbent assembly 44 that includes at least one component that is treated with a hydrophobically modified polymer, such that upon entering into an aqueous solution created by an insult of a body exudate, the hydrophobically modified polymer is configured to interact with a surfactant that entered into the aqueous solution to increase the surface tension of the aqueous solution to reduce the likelihood for re-wet or leaks from the absorbent article 10 and/or absorbent assembly 44. It is contemplated that only one component may be treated with hydrophobically modified polymer, however, it is also contemplated that more than one component of the absorbent article 10 or absorbent assembly 44 is treated with one or more hydrophobically modified polymers. Each example is provided by way of explanation and is not meant as a limitation. For example, features illustrated or described as part of one embodiment or figure can be used on another embodiment or figure to yield yet another embodiment. It is intended that the present disclosure include such modifications and variations.

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention.

Definitions:

The term "absorbent article" refers herein to an article which may be placed against or in proximity to the body (i.e., contiguous with the body) of the wearer to absorb and contain various liquid, solid, and semi-solid exudates discharged from the body. Such absorbent articles, as described herein, are intended to be discarded after a limited period of use instead of being laundered or otherwise restored for reuse. It is to be understood that the present disclosure is applicable to various disposable absorbent articles, including, but not limited to, diapers, diaper pants, training pants, youth pants, swim pants, feminine hygiene products, including, but not limited to, menstrual pads or pants, incontinence products, medical garments, surgical pads and bandages, other personal care or health care garments, and the like without departing from the scope of the present disclosure.

The term "acquisition layer" refers herein to a layer capable of accepting and temporarily holding liquid body exudates to decelerate and diffuse a surge or gush of the liquid body exudates and to subsequently release the liquid body exudates therefrom into another layer or layers of the absorbent article.

The term "bonded" or "coupled" refers herein to the joining, adhering, connecting, attaching, or the like, of two elements. Two elements will be considered bonded or coupled together when they are joined, adhered, connected, attached, or the like, directly to one another or indirectly to one another, such as when each is directly bonded to intermediate elements. The bonding or coupling of one element to another can occur via continuous or intermittent bonds.

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. Such webs are usually subjected to some type of bonding process such as thermal bonding using heat and/or pressure. In addition to or in lieu thereof, the fibers may be subject to adhesive processes to bind the fibers together such as by the use of powder adhesives. The carded web may be subjected to fluid entangling, such as hydroentangling, to further intertwine the fibers and thereby improve the integrity of the carded web. Carded webs, due to the fiber alignment in the machine direction, once bonded, will typically have more machine direction strength than cross machine direction strength.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films.

The term "gsm" refers herein to grams per square meter.

The term "hydrophilic" refers herein to fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "hydrophobically modified polymer" ("HMP") refers herein to a water-soluble polymer which has hydrophobic chains installed onto a polymeric backbone, where the hydrophobic chains can serve as templates for binding other hydrophobic moieties using van der Waal's interactions.

The term "liquid impermeable" refers herein to a layer or multi-layer laminate in which liquid body exudates, such as urine, will not pass through the layer or laminate, under ordinary use conditions, in a direction generally perpendicular to the plane of the layer or laminate at the point of liquid contact.

The term "liquid permeable" refers herein to any material that is not liquid impermeable.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

The term "pliable" refers herein to materials which are compliant and which will readily conform to the general shape and contours of the wearer's body.

The term "spunbond" refers herein to small diameter fibers which are formed by extruding molten thermoplastic material as filaments from a plurality of fine capillaries of a spinnerette having a circular or other configuration, with the diameter of the extruded filaments then being rapidly reduced by a conventional process such as, for example, eductive drawing, and processes that are described in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Peterson, and U.S. Pat. No. 3,542,615 to Dobo et al., each of which is incorporated herein in its entirety by reference. Spunbond fibers are generally continuous and often have average deniers larger than about 0.3, and in an embodiment, between about 0.6, 5 and 10 and about 15, 20 and 40. Spunbond fibers are generally not tacky when they are deposited on a collecting surface.

The term "superabsorbent" refers herein to a water-swellable, water-insoluble organic or inorganic material capable, under the most favorable conditions, of absorbing at least about 15 times its weight and, in an embodiment, at least about 30 times its weight, in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds, such as cross-linked polymers.

The term "thermoplastic" refers herein to a material which softens and which can be shaped when exposed to heat and which substantially returns to a non-softened condition when cooled.

The term "user" or "caregiver" refers herein to one who fits an absorbent article, such as, but not limited to, a diaper, diaper pant, training pant, youth pant, incontinent product, or other absorbent article about the wearer of one of these absorbent articles. A user and a wearer can be one and the same person.

Figure 2:
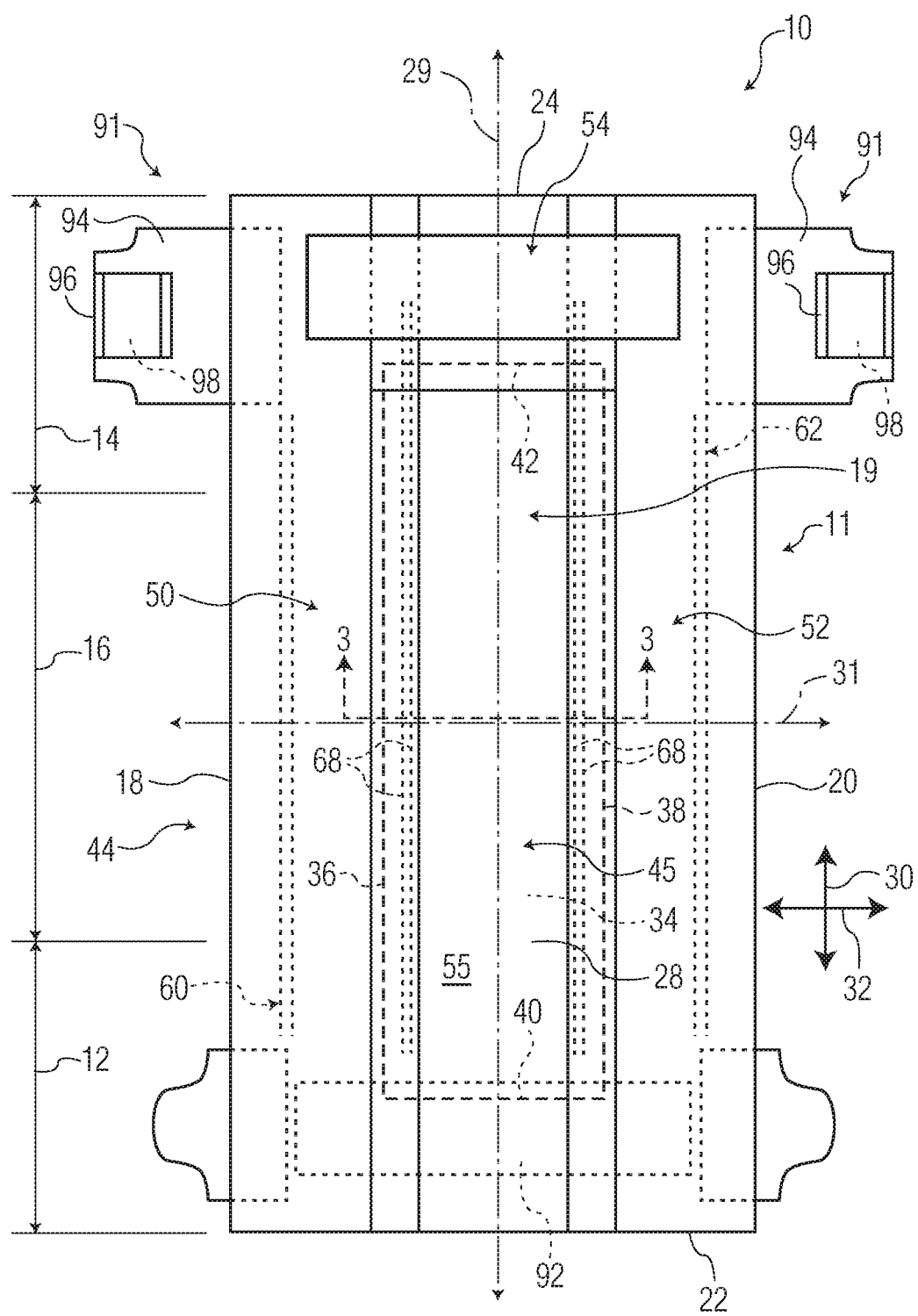
FIG. 2 is a top plan view of the absorbent article of FIG. 1 in a stretched, laid flat, unfastened condition.
Figure 3:
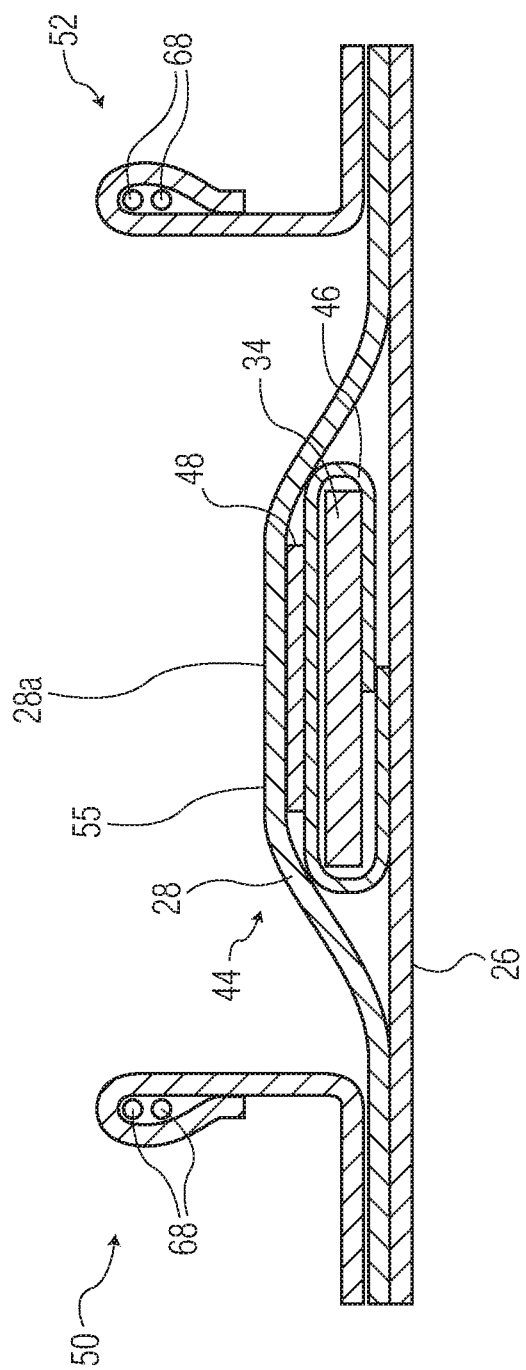
FIG. 3 is a cross-sectional view taken along line 3-3 from FIG. 2, with the absorbent article being in a relaxed configuration.

Absorbent Article:

Referring to FIGS. 1-3, a non-limiting illustration of an absorbent article 10, for example, a diaper, is illustrated. However, other embodiments of an absorbent article 10 could include training pants, diaper pants, youth pants, adult incontinence garments, and feminine hygiene articles, among others. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

The absorbent article 10 illustrated in FIGS. 1-3 can include a chassis 11. The absorbent article 10 can include a front waist region 12, a rear waist region 14, and a crotch region 16 disposed between the front waist region 12 and the rear waist region 14 and interconnecting the front and rear waist regions, 12, 14, respectively. The front waist region 12 can be referred to as the front end region, the rear waist region 14 can be referred to as the rear end region, and the crotch region 16 can be referred to as the intermediate region.

The absorbent article 10 can have a pair of longitudinal side edges 18, 20, and a pair of opposite waist edges, respectively designated front waist edge 22 and rear waist edge 24. The front waist region 12 can be contiguous with the front waist edge 22 and the rear waist region 14 can be contiguous with the rear waist edge 24. The longitudinal side edges 18, 20 can extend from the front waist edge 22 to the rear waist edge 24. The longitudinal side edges 18, 20 can extend in a direction parallel to the longitudinal direction 30 for their entire length, such as for the absorbent article 10 illustrated in FIG. 2. In other embodiments, the longitudinal side edges 18, 20 can be curved between the front waist edge 22 and the rear waist edge 24.

The front waist region 12 can include the portion of the absorbent article 10 that, when worn, is positioned at least in part on the front of the wearer while the rear waist region 14 can include the portion of the absorbent article 10 that, when worn, is positioned at least in part on the back of the wearer. The crotch region 16 of the absorbent article 10 can include the portion of the absorbent article 10 that, when worn, is positioned between the legs of the wearer and can partially cover the lower torso of the wearer. The waist edges, 22 and 24, of the absorbent article 10 are configured to encircle the waist of the wearer and together define a central waist opening 23 (as labeled in FIG. 1) for the waist of the wearer. Portions of the longitudinal side edges 18, 20 in the crotch region 16 can generally define leg openings for the legs of the wearer when the absorbent article 10 is worn.

The absorbent article 10 can include an outer cover 26 and a bodyside liner 28. The outer cover 26 and the bodyside liner 28 can form a portion of the chassis 11. In an embodiment, the bodyside liner 28 can be bonded to the outer cover 26 in a superposed relation by any suitable means such as, but not limited to, adhesives, ultrasonic bonds, thermal bonds, pressure bonds, or other conventional techniques. The outer cover 26 can define a length in a longitudinal direction 30, and a width in the lateral direction 32, which, in the illustrated embodiment, can coincide with the length and width of the absorbent article 10. As illustrated in FIG. 2, the absorbent article 10 can have a longitudinal axis 29 extending in the longitudinal direction 30 and a lateral axis 31 extending in the lateral direction 32.

The chassis 11 can include an absorbent assembly 44. The absorbent assembly 44 can include an absorbent body 34. The absorbent body 34 can be disposed between the outer cover 26 and the bodyside liner 28. The absorbent body 34 can have longitudinal edges, 36 and 38, which, in an embodiment, can form portions of the longitudinal side edges, 18 and 20, respectively, of the absorbent article 10. The absorbent body 34 can have a first end edge 40 that is opposite a second end edge 42, respectively, which, in an embodiment, can form portions of the waist edges, 22 and 24, respectively, of the absorbent article 10. In some embodiments, the first end edge 40 can be in the front waist region 12. In some embodiments, the second end edge 42 can be in the rear waist region 14. In an embodiment, the absorbent body 34 can have a length and width that are the same as or less than the length and width of the absorbent article 10. The bodyside liner 28 and the outer cover 26 can also form part of the absorbent assembly 44. The absorbent assembly 44 can also include a fluid transfer layer 46 (as illustrated in FIG. 3) in some embodiments. The fluid transfer layer 46, if present, can at least partially envelope the absorbent body 34. In some embodiments, the absorbent assembly 44 can also include a fluid acquisition layer 48 (depicted in FIG. 3). The fluid acquisition layer 48 can be disposed between the bodyside liner 28 and the absorbent body 34. In embodiments including a fluid transfer layer 46, the acquisition layer 48 can be disposed between the bodyside liner 28 and the fluid transfer layer 46. The absorbent assembly 44 can also include a spacer layer (not shown) disposed between the absorbent body 34 and the outer cover 26 as is known in the art. The absorbent assembly 44 can include other components in some embodiments. It is also contemplated that some embodiments may not include a fluid transfer layer 46, and/or an acquisition layer 48, and/or a spacer layer.

The absorbent article 10 can be configured to contain and/or absorb liquid, solid, and semi-solid body exudates discharged from the wearer. In some embodiments, a pair of containment flaps 50, 52 can be configured to provide a barrier to the lateral flow of body exudates. In some embodiments, the absorbent article 10 can include a waist containment member 54. The waist containment member 54 can be disposed in the rear waist region 14 of the absorbent article 10. Although not depicted herein, it is contemplated that the waist containment member 54 can be additionally or alternatively disposed in the front waist region 12 of the absorbent article 10.

The absorbent article 10 can further include leg elastic members 60, 62 as are known to those skilled in the art. The leg elastic members 60, 62 can be attached to the outer cover 26 and/or the bodyside liner 28 along the opposite longitudinal side edges, 18 and 20, and positioned in the crotch region 16 of the absorbent article 10. The leg elastic members 60, 62 can be parallel to the longitudinal axis 29 as shown in FIG. 2 or can be curved as is known in the art. The leg elastic members 60, 62 can provide elasticized leg cuffs.

Additional details regarding each of these elements of the absorbent article 10 described herein can be found below and with reference to the Figures.

Outer cover:

The outer cover 26 and/or portions thereof can be breathable and/or liquid impermeable. The outer cover 26 and/or portions thereof can be elastic, stretchable, or non-stretchable. The outer cover 26 may be constructed of a single layer, multiple layers, laminates, spunbond fabrics, films, meltblown fabrics, elastic netting, microporous webs, bonded-carded webs or foams provided by elastomeric or polymeric materials. In an embodiment, for example, the outer cover 26 can be constructed of a microporous polymeric film, such as polyethylene or polypropylene.

In an embodiment, the outer cover 26 can be a single layer of a liquid impermeable material, such as a polymeric film. In an embodiment, the outer cover 26 can be suitably stretchable, and more suitably elastic, in at least the lateral direction 32 of the absorbent article 10. In an embodiment, the outer cover 26 can be stretchable, and more suitably elastic, in both the lateral 32 and the longitudinal 30 directions. In an embodiment, the outer cover 26 can be a multi-layered laminate in which at least one of the layers is liquid impermeable. In some embodiments, the outer cover 26 can be a two layer construction, including an outer layer (not shown) and an inner layer (not shown) which can be bonded together such as by a laminate adhesive. Suitable laminate adhesives can be applied continuously or intermittently as beads, a spray, parallel swirls, or the like, but it is to be understood that the inner layer can be bonded to the outer layer by other bonding methods, including, but not limited to, ultrasonic bonds, thermal bonds, pressure bonds, or the like.

The outer layer of the outer cover 26 can be any suitable material and may be one that provides a generally cloth-like texture or appearance to the wearer. An example of such material can be a 100% polypropylene bonded-carded web with a diamond bond pattern available from Sandler A. G., Germany, such as 30 gsm Sawabond 4185® or equivalent. Another example of material suitable for use as an outer layer of an outer cover 26 can be a 20 gsm spunbond polypropylene non-woven web. The outer layer may also be constructed of the same materials from which the bodyside liner 28 can be constructed as described herein.

The liquid impermeable inner layer of the outer cover 26 (or the liquid impermeable outer cover 26 where the outer cover 26 is of a single-layer construction) can be either vapor permeable (i.e., "breathable") or vapor impermeable. The liquid impermeable inner layer (or the liquid impermeable outer cover 26 where the outer cover 26 is of a single-layer construction) can be manufactured from a thin plastic film. The liquid impermeable inner layer (or the liquid impermeable outer cover 26 where the outer cover 26 is of a single-layer construction) can inhibit liquid body exudates from leaking out of the absorbent article 10 and wetting articles, such as bed sheets and clothing, as well as the wearer and caregiver.

In some embodiments, where the outer cover 26 is of a single layer construction, it can be embossed and/or matte finished to provide a more cloth-like texture or appearance. The outer cover 26 can permit vapors to escape from the absorbent article 10 while preventing liquids from passing through. A suitable liquid impermeable, vapor permeable material can be composed of a microporous polymer film or a non-woven material which has been coated or otherwise treated to impart a desired level of liquid impermeability.

Bodyside liner:

The bodyside liner 28 of the absorbent article 10 can overlay the absorbent body 34 and the outer cover 26 and can be configured to receive insults of exudates from the wearer and can isolate the wearer's skin from liquid waste retained by the absorbent body 34. The bodyside liner 28 can form at least a part of the body facing surface 19 of the chassis 11.

In various embodiments, a fluid transfer layer 46 can be positioned between the bodyside liner 28 and the absorbent body 34 (as shown in FIG. 3). In various embodiments, an acquisition layer 48 can be positioned between the bodyside liner 28 and the absorbent body 34 or a fluid transfer layer 46, if present (as shown in FIG. 3). In various embodiments, the bodyside liner 28 can be bonded to the acquisition layer 48, or to the fluid transfer layer 46 if no acquisition layer 48 is present, via adhesive and/or by a point fusion bonding. The point fusion bonding may be selected from ultrasonic, thermal, pressure bonding, and combinations thereof.

In an embodiment, the bodyside liner 28 can extend beyond the absorbent body 34 and/or a fluid transfer layer 46, if present, and/or an acquisition layer 48, if present, and/or a spacer layer, if present, to overlay a portion of the outer cover 26 and can be bonded thereto by any method deemed suitable, such as, for example, by being bonded thereto by adhesive, to substantially enclose the absorbent body 34 between the outer cover 26 and the bodyside liner 28. In some embodiments, the bodyside liner 28 and the outer cover 26 may be of the same dimensions in width and length. In some embodiments, however, the bodyside liner 28 may be narrower than the outer cover 26 and/or shorter than the outer cover 26. For example, in some embodiments where the absorbent article includes a separate front panel and a rear panel (not shown), the bodyside liner 28 can extend between the front panel and the rear panel, but not all the way to the front waist edge 22 and the rear waist edge 24. In some embodiments, the length of the bodyside liner 28 can range from 50%-100% of the length of the absorbent article 10 as measured in a direction parallel to the longitudinal axis 29, and in some embodiments can range from 50%-95% of the length of the absorbent article 10 can range from 60%-90% of the length of the absorbent article 10. In some embodiments, the bodyside liner 28 can be of greater width than the outer cover 26. It is also contemplated that the bodyside liner 28 may not extend beyond the absorbent body 34 and/or may not be secured to the outer cover 26. In some embodiments, the bodyside liner 28 can wrap at least a portion of the absorbent body 34, including wrapping around both longitudinal edges 36, 38 of the absorbent body 34, and/or one or more of the end edges 40, 42. It is further contemplated that the bodyside liner 28 may be composed of more than one segment of material.

The bodyside liner 28 can be of different shapes, including rectangular, hourglass, or any other shape. The bodyside liner 28 can be suitably compliant, soft feeling, and non-irritating to the wearer's skin and can be the same as or less hydrophilic than the absorbent body 34 to permit body exudates to readily penetrate through to the absorbent body 34 and provide a relatively dry surface to the wearer.

The bodyside liner 28 can be manufactured from a wide selection of materials, such as synthetic fibers (for example, polyester or polypropylene fibers), natural fibers (for example, wood or cotton fibers), a combination of natural and synthetic fibers, porous foams, reticulated foams, apertured plastic films, or the like. Examples of suitable materials include, but are not limited to, rayon, wood, cotton, polyester, polypropylene, polyethylene, nylon, or other heat-bondable fibers, polyolefins, such as, but not limited to, copolymers of polypropylene and polyethylene, linear low-density polyethylene, and aliphatic esters such as polylactic acid, finely perforated film webs, net materials, and the like, as well as combinations thereof.

Various woven and non-woven fabrics can be used for the bodyside liner 28. The bodyside liner 28 can include a woven fabric, a nonwoven fabric, a polymer film, a film-fabric laminate or the like, as well as combinations thereof. Examples of a nonwoven fabric can include spunbond fabric, meltblown fabric, coform fabric, carded web, bonded-carded web, bicomponent spunbond fabric, spunlace, or the like, as well as combinations thereof. The bodyside liner 28 need not be a unitary layer structure, and thus, can include more than one layer of fabrics, films, and/or webs, as well as combinations thereof. For example, the bodyside liner 28 can include a support layer and a projection layer that can be hydroentagled. The projection layer can include hollow projections, such as those disclosed in U.S. Pat. No. 9,474,660 invented by Kirby, Scott S. C. et al. The bodyside liner 28 can also include a layer below such a support layer and projection layer.

In some embodiments, the bodyside liner 28 can be composed of a meltblown or spunbond web of polyolefin fibers. Alternatively, the bodyside liner 28 can be a bonded-carded web composed of natural and/or synthetic fibers. The bodyside liner 28 can be composed of a substantially hydrophobic material, and the hydrophobic material can, optionally, be treated with a surfactant or otherwise processed to impart a desired level of wettability and hydrophilicity.

The bodyside liner 28 can be treated with a surfactant to help the bodyside liner 28 have quicker intake of an aqueous solution provided by an insult of a body exudate to the absorbent assembly 44, including to the absorbent body 34. The bodyside liner 28 can be treated with the surfactant by, for example, applying the surfactant to the bodyside liner 28 by any conventional means, such as spraying, printing, brush coating or the like. The surfactant can be applied to the entire bodyside liner 28 or it can be selectively applied to particular sections of the bodyside liner 28. For example, a surfactant can be applied to the body-facing surface 28a (see FIG. 3) of the bodyside liner 28. Further discussion of the various classes of and specific examples of surfactants that can be utilized and that were tested herein are described further below.

Additionally, in some embodiments, the bodyside liner 28 can be treated with a hydrophobically modified polymer (HMP). The bodyside liner 28 can be treated with the HMP by, for example, applying the HMP to the bodyside liner 28 by any conventional means, such as spraying, printing, brush coating or the like. Further discussion of the various classes of and specific examples of HMPs that can be utilized and that were tested herein are described further below.

In an embodiment, a bodyside liner 28 can be constructed of a non-woven bicomponent web. The non-woven bicomponent web can be a spunbonded bicomponent web, or a bonded-carded bicomponent web. An example of a bicomponent staple fiber includes a polyethylene/polypropylene bicomponent fiber. In this particular bicomponent fiber, the polypropylene forms the core and the polyethylene forms the sheath of the fiber. Fibers having other orientations, such as multi-lobe, side-by-side, end-to-end may be used without departing from the scope of this disclosure. In an embodiment, a bodyside liner 28 can be a spunbond substrate with a basis weight from about 10 or 12 to about 15 or 20 gsm. In an embodiment, a bodyside liner 28 can be a 12 gsm spunbond-meltblown-spunbond substrate having 10% meltblown content applied between the two spunbond layers.

Although the outer cover 26 and bodyside liner 28 can include elastomeric materials, it is contemplated that the outer cover 26 and the bodyside liner 28 can be composed of materials which are generally non-elastomeric. In an embodiment, the bodyside liner 28 can be stretchable, and more suitably elastic. In an embodiment, the bodyside liner 28 can be suitably stretchable and more suitably elastic in at least the lateral or circumferential direction of the absorbent article 10. In other aspects, the bodyside liner 28 can be stretchable, and more suitably elastic, in both the lateral and the longitudinal directions 32, 30, respectively.

Absorbent Body:

The absorbent body 34 can be suitably constructed to be generally compressible, conformable, pliable, non-irritating to the wearer's skin and capable of absorbing and retaining liquid body exudates. The absorbent body 34 can be manufactured in a wide variety of sizes and shapes (for example, rectangular, trapezoidal, T-shape, I-shape, hourglass shape, etc.) and from a wide variety of materials. The size and the absorbent capacity of the absorbent body 34 should be compatible with the size of the intended wearer (infants to adults) and the liquid loading imparted by the intended use of the absorbent article 10. The absorbent body 34 can have a length and width that can be less than or equal to the length and width of the absorbent article 10.

In an embodiment, the absorbent body 34 can be composed of a web material of hydrophilic fibers, cellulosic fibers (e.g., wood pulp fibers), natural fibers, synthetic fibers, woven or nonwoven sheets, scrim netting or other stabilizing structures, superabsorbent material, binder materials, surfactants, selected hydrophobic and hydrophilic materials, pigments, lotions, odor control agents or the like, as well as combinations thereof. In an embodiment, the absorbent body 34 can be a matrix of cellulosic fluff and superabsorbent material. In an embodiment, the absorbent body 34 may be constructed of a single layer of materials, or in the alternative, may be constructed of two or more layers of materials.

Various types of wettable, hydrophilic fibers can be used in the absorbent body 34. Examples of suitable fibers include natural fibers, cellulosic fibers, synthetic fibers composed of cellulose or cellulose derivatives, such as rayon fibers; inorganic fibers composed of an inherently wettable material, such as glass fibers; synthetic fibers made from inherently wettable thermoplastic polymers, such as particular polyester or polyamide fibers, or composed of nonwettable thermoplastic polymers, such as polyolefin fibers which have been hydrophilized by suitable means. The fibers may be hydrophilized, for example, by treatment with a surfactant, treatment with silica, treatment with a material which has a suitable hydrophilic moiety and is not readily removed from the fiber, or by sheathing the nonwettable, hydrophobic fiber with a hydrophilic polymer during or after formation of the fiber. Suitable superabsorbent materials can be selected from natural, synthetic, and modified natural polymers and materials. The superabsorbent materials can be inorganic materials, such as silica gels, or organic compounds, such as cross-linked polymers. In an embodiment, the absorbent body 34 can be free of superabsorbent material.

In some embodiments, the absorbent body 34 can be treated with an HMP. The absorbent body 34 can be treated with an HMP by, for example, applying the HMP to the absorbent body 34 by any conventional means, such as spraying, printing, brush coating or the like.

If a spacer layer is present, the absorbent body 34 can be disposed on the spacer layer and superposed over the outer cover 26. The spacer layer can be bonded to the outer cover 26, for example, by adhesive. In some embodiments, a spacer layer may not be present and the absorbent body 34 can directly contact the outer cover 26 and can be directly bonded to the outer cover 26. However, it is to be understood that the absorbent body 34 may be in contact with, and not bonded with, the outer cover 26 and remain within the scope of this disclosure. In an embodiment, the outer cover 26 can be composed of a single layer and the absorbent body 34 can be in contact with the singer layer of the outer cover 26. In some embodiments, at least a portion of a layer, such as but not limited to, a fluid transfer layer 46 and/or a spacer layer, can be positioned between the absorbent body 34 and the outer cover 26. The absorbent body 34 can be bonded to the fluid transfer layer 46 and/or the spacer layer. In some embodiments, the fluid transfer layer 46 can Containment Flaps:

In an embodiment, the absorbent article 10 can include a pair of containment flaps 50, 52. The containment flaps 50, 52 can be formed separately from the absorbent chassis 11 and attached to the chassis 11 or can be formed integral to the chassis 11. In some embodiments, the containment flaps 50, 52 can be secured to the chassis 11 of the absorbent article 10 in a generally parallel, spaced relation with each other laterally inward of the leg openings to provide a barrier against the flow of body exudates. One containment flap 50 can be on a first side of the longitudinal axis 29 and the other containment flap 52 can be on a second side of the longitudinal axis 29. In an embodiment, the containment flaps 50, 52 can extend generally in a longitudinal direction 30 from the front waist region 12 of the absorbent article 10 through the crotch region 16 to the rear waist region 14 of the absorbent article 10. In some embodiments, the containment flaps 50, 52 can extend in a direction substantially parallel to the longitudinal axis 29 of the absorbent article 10, however, in other embodiments, the containment flaps 50, 52 can be curved, as is known in the art.

In embodiments where the containment flaps 50, 52 are coupled to the chassis 11, the containment flaps 50, 52 can be bonded to the bodyside liner 28, the outer cover 26, or another layer, such as a spacer layer, if present, with a barrier adhesive, as is known in the art. Of course, the containment flaps 50, 52 can be bonded to other components of the chassis 11 and can be bonded with other suitable means other than a barrier adhesive. For example, the containment flaps 50, 52 can be bonded to the bodyside liner 28, the outer cover 26, or another layer with pressure bonding, thermal bonding, or ultrasonic bonding. The containment flaps 50, 52 can be constructed of a fibrous material which can be similar to the material forming the bodyside liner 28. Other conventional materials, such as polymer films, can also be employed.

The containment flaps 50, 52 can include one or more flap elastic members 68, such as the two flap elastic strands depicted in FIGS. 2 and 3. Suitable elastic materials for the flap elastic members 68 can include sheets, strands or ribbons of natural rubber, synthetic rubber, or thermoplastic elastomeric materials. Of course, while two elastic members 68 are shown in each containment flap 50, 52, it is contemplated that the containment flaps 50, 52 can be configured with one or three or more elastic members 68. Alternatively or additionally, the containment flaps 50, 52 can be composed of a material exhibiting elastic properties itself.

The flap elastic members 68, as illustrated in FIG. 2, can have two strands of elastomeric material extending longitudinally in a projection portion of the containment flaps 50, 52, in generally parallel, spaced relation with each other. The flap elastic members 68 can be within the containment flaps 50, 52 while in an elastically contractible condition such that contraction of the strands gathers and shortens the containment flaps 50, 52 in the longitudinal direction 30. As a result, the elastic members 68 can bias the containment flaps 50, 52 to extend away from the body facing surface 45 of the absorbent assembly 44 in a generally upright orientation of the containment flaps 50, 52, especially in the crotch region 16 of the absorbent article 10 when the absorbent article 10 is in a relaxed configuration, such as demonstrated in FIG. 3.

During manufacture of the containment flaps 50, 52 at least a portion of the elastic members 68 can be bonded to the containment flaps 50, 52 while the elastic members 68 are elongated. The percent elongation of the elastic members 68 can be, for example, about 110% to about 350%. In one embodiment, the elastic members 68 can be coated with adhesive while elongated to a specified length prior to attaching to the elastic members 68 to the containment flaps 50, 52. In this exemplary method of bonding the elastic members 68 to the containment flaps 50, 52, the portion of the elastic members 68 not coated with adhesive, will retract after the elastic members 68 and the absorbent article 10 are cut in manufacturing to form an individual absorbent article 10. As noted above, the relaxing of the elastic members 68 when the absorbent article 10 is in a relaxed condition can cause each containment flap 50, 52 to gather and cause a portion of each containment flap 50, 52 to extend away from the body facing surface 19 of the chassis 11 (e.g., the body facing surface 45 of the absorbent assembly 44 or the body facing surface 55 of the bodyside liner 28).

Of course, the elastic members 68 can be bonded to the containment flaps 50, 52 in various other ways as known by those of skill in the art, which is within the scope of this disclosure.

Leg Elastics:

Leg elastic members 60, 62 can be secured to the outer cover 26, such as by being bonded thereto by laminate adhesive, generally laterally inward of the longitudinal side edges, 18 and 20, of the absorbent article 10. The leg elastic members 60, 62 can form elasticized leg cuffs that further help to contain body exudates. In an embodiment, the leg elastic members 60, 62 may be disposed between inner and outer layers (not shown) of the outer cover 26 or between other layers of the absorbent article 10, for example, between the containment flaps 50, 52 and the bodyside liner 28, between the containment flap 50, 52 and the outer cover 26, or between the bodyside liner 28 and the outer cover 26. The leg elastic members 60, 62 can be one or more elastic components near each longitudinal side edge 18, 20. For example, the leg elastic members 60, 62 as illustrated herein in FIG. 2 each include two elastic strands. A wide variety of elastic materials may be used for the leg elastic members 60, 62. Suitable elastic materials can include sheets, strands or ribbons of natural rubber, synthetic rubber, or thermoplastic elastomeric materials. The elastic materials can be stretched and secured to a substrate, secured to a gathered substrate, or secured to a substrate and then elasticized or shrunk, for example, with the application of heat, such that the elastic retractive forces are imparted to the substrate. Additionally, it is contemplated that the leg elastic members 60, 62 can be formed with the containment flaps 50, 52, and then attached to the chassis 11 in some embodiments. Of course, the leg elastic members 60, 62 can be omitted from the absorbent article 10 without departing from the scope of this disclosure.

Waist Containment Member:

In an embodiment, the absorbent article 10 can have one or more waist containment members 54. FIGS. 1 and 2 illustrate an embodiment of a waist containment member 54 on an absorbent article 10, such as a diaper. The waist containment member 54 can be disposed in the rear waist region 14, while in some embodiments, the waist containment member 54 can be disposed in the front waist region 12. The waist containment member 54 can be disposed on the body facing surface 45 of the absorbent assembly 44. In some embodiments, such as in the embodiment illustrated in FIGS. 1 and 2, the waist containment member 54 can be disposed on the body facing surface 55 of the bodyside liner 28. The waist containment member 54 can be coupled to the chassis 11 such that a portion 54a of the waist containment member 54 is free to move with respect to the chassis 11 and can form a pocket to help contain body exudates.

The waist containment member 54 can be comprised of a variety of materials. In a preferred embodiment, the waist containment member 54 can be comprised of a spunbond-meltblown-spunbond ("SMS") material. However it is contemplated that the waist containment member 54 can be comprised of other materials including, but not limited to, a spunbond-film-spunbond ("SFS"), a bonded carded web ("BCW"), or any non-woven material. In some embodiments, the waist containment member 54 can be comprised of a laminate of more than one of these exemplary materials, or other materials. In some embodiments, the waist containment member 54 can be comprised of a liquid impermeable material. In some embodiments, the waist containment member 54 can be comprised of a material coated with a hydrophobic coating. In some embodiments, the waist containment member 54 can include an elastic material to provide additional fit and containment properties to the absorbent article 10. In such an embodiment, suitable elastic materials can include, but are not limited to, sheets, strands or ribbons of natural rubber, synthetic rubber, or thermoplastic elastomeric polymers. The elastic materials can be stretched and bonded to a substrate, bonded to a gathered substrate, or bonded to a substrate and then elasticized or shrunk, for example, with the application of heat, such that elastic retractive forces are imparted to the substrate. It is to be understood, however, that the waist containment member 54 may be omitted from the absorbent article without departing from the scope of this disclosure.

Fastening System:

In an embodiment, the absorbent article 10 can include a fastening system. The fastening system can include one or more back fasteners 91 and one or more front fasteners 92. The embodiment shown in FIGS. 1 and 2 depict an embodiment with one front fastener 92. Portions of the fastening system may be included in the front waist region 12, rear waist region 14, or both.

The fastening system can be configured to secure the absorbent article 10 about the waist of the wearer in a fastened condition as shown in FIG. 1 and help maintain the absorbent article 10 in place during use. In an embodiment, the back fasteners 91 can include one or more materials bonded together to form a composite ear as is known in the art. For example, the composite fastener may be composed of a stretch component 94, a nonwoven carrier or hook base 96, and a fastening component 98, as labeled in FIG. 2.

Surfactants and Hydrophobically Modified
Polymers

As previously noted, one or more components of the absorbent article 10 and/or absorbent assembly 44 may be treated with a surfactant to help reduce the surface tension of the aqueous solution that can be created by body exudates, such as urine, feces, menses, etc, and improve intake of such an aqueous solution into the absorbent article 10 and the absorbent assembly 44. As the aqueous solution flows over the component(s) treated with the surfactant, the surfactant can become incorporated into the aqueous solution and provide the reduced surface tension properties for that solution of body exudates. Some embodiments of the present disclosure have a bodyside liner 28 that is treated with a surfactant. However, other components of the absorbent article 10 may additionally or alternatively be treated with a surfactant.

Surfactants are molecules that are composed of a hydrophilic group and a hydrophobic group. When they are dispersed in water they lower the surface tension by disrupting the hydrogen bonds created between water molecules. When a surfactant is in a solution and contacts a substrate, the surfactant can decrease the contact angle of the solution in which they are in, allowing for increased wetting behavior. Surfactants naturally migrate to a liquid-liquid interface until it is saturated. Once the interface is saturated, the surfactants arrange themselves in micelles. A micelle is a grouping of surfactants that have aligned so that the hydrophilic portion is facing the water phase and the hydrophobic portions are aligned inwards in a spherical shape. When micelles begin to form at a specific concentration of surfactant within a solution, that is referred to as the Critical Micelle Concentration (CMC).

Once the CMC is reached, the surface tension of such a solution is at its lowest attainable value for that surfactant. Surface tension can be measured at the interface of two liquids or in the bulk of a liquid. The equilibrium surface tension of a liquid is the ability of surfactants to reduce surface tension at the interface after the surfactants are able to completely saturate the interface. The dynamic surface tension is measured within the bulk of the fluid. It is the surface tension of a newly developed surface after a measured amount of time, when the surfactant is still in the process of migrating to the interface. Dynamic surface tension can be measured using a bubble tensiometer. The device creates a bubble and calculates surface tension based on the maximum bubble pressure. It does this at a set lifetime of the bubble. Equilibrium surface tension can be measured using a Wilhelmy plate tensiometer, and is the surface tension measured in the Surface Tension Test Method described in the Test Methods section herein. Equilibrium surface tension is a measure of the surface tension when the surfactant has had substantial time to migrate to the interface.

Four classes of surfactants that were reviewed and tested herein include: nonionic surfactants, anionic surfactants, cationic surfactants, and zwitterionic surfactants. The surfactants that were tested herein are listed in Table 1.

TABLE 1

| | List of surfactants | | | |
|---|---|---|---|---|
| Surfactant Code No. | INCI Name | Class | Trade Name Example | Manufacturer |
| A | Sodium Laurel Ether Sulfate (SLES) | anionic | Colonial SLES-2 | Colonial Chemical, Inc. |
| B | Laureth-23 | ethoxylate | BRIJ L 23 | Croda Inc. |
| C | Polyalkyleneoxidemethylsiloxane copolymer | silicon based | Silwet* DA-63 | Momentive Performance Materials |
| D | Unknown | Unknown | Sanoil 884 | Sanyo Corp. |
| E | Unknown | Unknown | Silastol 163 | Schill and Seilacher |
| F | Polysorbate 20 | non-ionic | Tween 20 | Sigma Aldrich |
| G | Cocamide DIPA | non-ionic | Cola Liquid DC | Colonial Chemical, Inc. |
| H | PEG-7 glyceryl cocoate | non-ionic | Glycerox HE | Croda Inc. |
| I | Decyl glucoside | non-ionic | Plantaren 2000 N UP | BASF |
| J | Caprylyl/capryl glucoside | non-ionic | Plantaren 810 UP | BASF |
| K | PEG-6 caprylic/capric glycerides | non-ionic | Tegosoft GMC-6 | Evonik Industries AG Personal Care |
| L | Perfluorononylethyl carboxydecyl PEG-10 dimethicone | non-ionic | Pecosil FDM-30 | Phoenix Chemical, Inc. |
| M | Laurylglucosides hydroxypropylsulfonate | anionic | Suga Nate 160 | Colonial Chemical, Inc. |
| N | Cetyl phosphate | anionic | Amphisol A | DSM Nutritional Products, LLC |
| O | Sodium lauryl sulfate | anionic | Calfoam SLS-30 | Pilot Chemical |
| P | Cetytrimethyl ammonium bromide | cationic | Rhodaquat M-242B/99 | Solvay Novecare |
| Q | PEG-15 cocomonium chloride | cationic | Maquat C-15 | Pilot Chemical |
| R | Polyquat 10 | cationic | UCARE JR 400 | The Dow Chemical Company |
| S | Alkyl polyethoxy phosphate ether | cationic | Dermalcare MAP-L-130 | Solvay Novecare |
| T | Sodium bis-hydroxyethylglycinate lauryl-glucosides copolymer | zwitterionic | Poly Suga Betaine L | Colonial Chemical, Inc. |
| U | Alkyl-betaine | zwitterionic | Mackam CB-35 | Solvay Novecare |
| V | Cocamidopropyl betaine | zwitterionic | Mackam 35 | Solvay Novecare |

In another aspect of this disclosure, one or more components of the absorbent article 10 and/or the absorbent assembly 44 can be treated with an HMP. For example, in preferred embodiments, one or more components of the absorbent article 10, such as a bodyside liner 28, a fluid acquisition layer 48, a fluid distribution layer 46, and/or an absorbent body 34, may be treated with an HMP. As mentioned above, an HMP can become incorporated into an aqueous solution by an insult of a body exudate flowing over the component of the absorbent article 10 or absorbent assembly 44 that was treated with the HMP, just as a surfactant is when the absorbent article 10 is insulted by a wearer. As surfactants have a hydrophobic tail, they are attracted towards the hydrophobic chains of HMPs and can end up bound to them. Although not to be bound by theory, it is believed that HMPs can associate with each other and other molecules in an aqueous solution including a surfactant, and it is believed that the HMP can bind the surfactants enough to increase the surface tension of such aqueous solution in comparison to that solution without the HMP. HMP backbones can include any of the following monomer types: polyvinylpyrrolidone, cellulose, acrylate, urethane, and polyquaternium.

Figure 4:
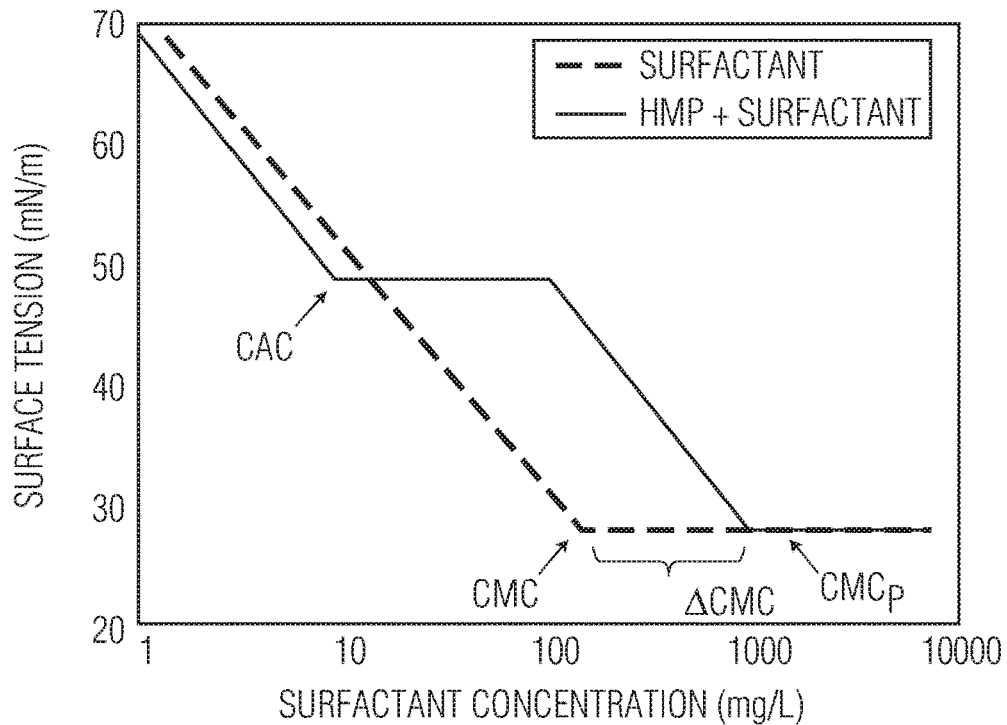
FIG. 4 is graph illustrating the idealized trend for surface tension vs. surfactant concentration for a surfactant solution in comparison with a solution including a surfactant and a hydrophobically modified polymer.

Various different HMPs were reviewed and tested herein and are listed in Table 2.

of surface tension as the solution with only a surfactant, even though the solution also has HMPs in it. As surfactant is continuously added, the surface tension begins to decrease until it reaches the Critical Aggregate Concentration (CAC). The CAC is the point at which the concentration of surfactant is high enough that the HMPs and surfactant molecules begin to interact and form micelle-like structures off of the hydrophobic tails on the HMP backbone. As the surfactant concentration increases from the point CAC is reached, until the HMP can no longer bind anymore surfactant molecules, the surface tension remains constant, as depicted in FIG. 4. Once the HMP can no longer bond anymore of the surfactant molecules, however, the addition of more surfactant results in a similar decrease in surface tension until the solution reaches an adjusted CMC ($CMC_P$), which occurs at the same surface tension as the solution including only surfactant (the dashed line), but at a higher concentration of the surfactant. The difference between the CMC for the surfactant solution (dashed line) and the adjusted $CMC_P$ for the solution including surfactant and an HMP (solid line) is illustrated as the change in CMC ($\Delta$ CMC) between the two solutions in FIG. 4.

The CAC is important because the HMP cannot start binding any of the surfactant molecules until the CAC is reached. Because of this, the highest surface tension that can

TABLE 2

List of HMPs

| HMP Code No. | INCI Name | Class | Trade Name Example | Manufacturer |
| --- | --- | --- | --- | --- |
| 1 | Experimental 1 (EXP. 1) | — | — | — |
| 2 | Experimental 2 (EXP. 2) | — | — | — |
| 3 | Experimental 3 (EXP. 3) | — | — | — |
| 4 | Experimental 4 (EXP. 4) | — | — | — |
| 5 | Experimental 5 (EXP. 5) | — | — | — |
| 6 | VP/acrylates/lauryl methacrylate copolymer | acrylate | Ganex Sensory Polymer | Ashland Chemical |
| 7 | Polyquaternium-55 | polyquaternium | Styleze W-17 | Ashland Chemical |
| 8 | Polyvinylpyrrolidone | cellulosic | Luviskol K 90 | BASF |
| 9 | Hydroxylethylcellulose | cellulosic | Natrosol 250 HHR CS | Ashland Chemical |
| 10 | Hydroxylethylcellulose | cellulosic | Natrosol Plus 330 | Ashland Chemical |
| 11 | Acrylates/vinyl neodecanoate crosspolymer | acrylate | Aculyn 38 | The Dow Chemical Company |
| 12 | PEG-150/stearyl alcohol/SMDI copolymer | urethane | Aculyn 46N | The Dow Chemical Company |
| 13 | Acrylates/beheneth-25 methacrylate copolymer | acrylate | Aculyn 28 | The Dow Chemical Company |
| 14 | Acrylates/steareth-20 methacrylate crosspolymer | acrylate | Aculyn 88 | The Dow Chemical Company |

FIG. 4 illustrates an idealized plot of surface tension vs. surfactant concentration. The dashed line on the plot is representative of an aqueous solution with a surfactant added. The solid line on the plot is an aqueous solution including the surfactant and an HMP. Looking first at the dashed line (the aqueous solution with only a surfactant added), as surfactant concentration increases, surface tension decreases up to a certain point known as the CMC. The CMC is the concentration at which, no matter how much more surfactant is added to the solution, the surface tension will not drop any further because the surface of the solution is as full as it can be, so the excess surfactant molecules begin forming micelles with themselves in solution.

Referring to the solid line (the aqueous solution including a surfactant and an HMP), it starts at virtually the same value be achieved using HMPs is the surface tension at CAC for that specific HMP and surfactant system. After HMPs are added to the system, the HMP molecules cannot pull surfactant molecules out enough to go above the CAC surface tension because, once it reduces the concentration of individual surfactant molecules to the CAC, the individual surfactant molecules and the HMP molecules no longer have any reason to interact. This makes CAC a key aspect in utilizing HMPs to quench a surfactant solution for surface tension reduction control.

A variety of Surface Tension tests were conducted to determine how much various combinations of surfactants and HMPs in aqueous solutions could modify the surface tension of such a solution in comparison to an aqueous solution including only the respective surfactant. The surface tension values depicted in FIGS. 5-17 were conducted according to the Surface Tension Test Method, as described in the Test Methods section herein.

Figure 5:
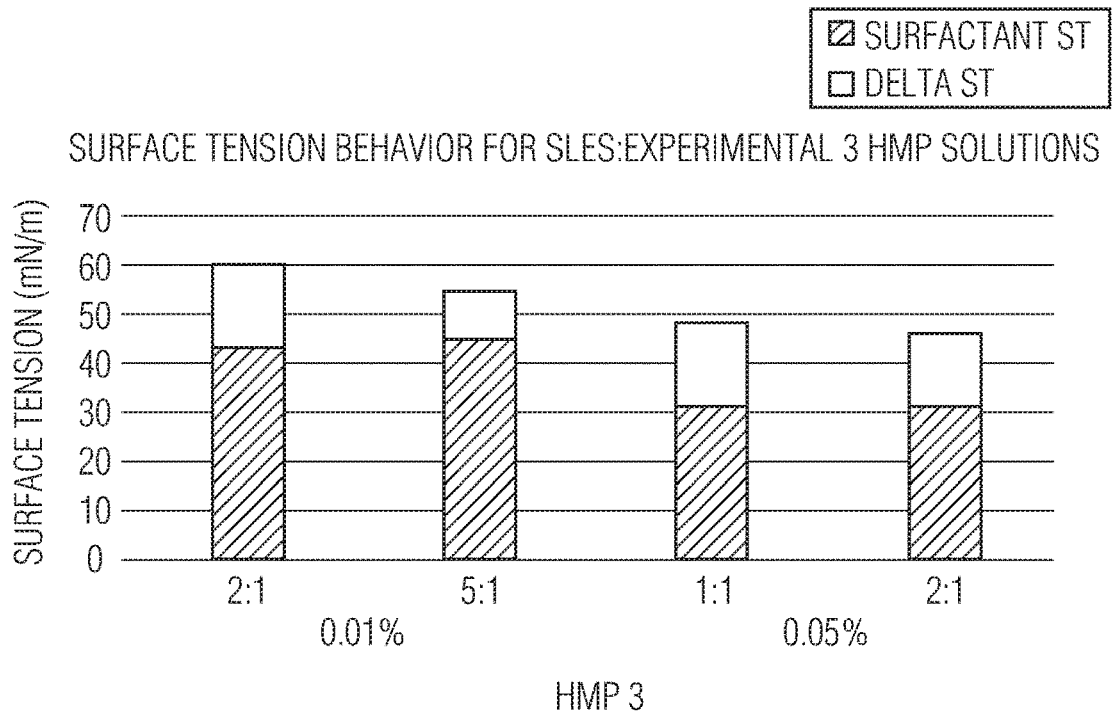
FIG. 5 is a graph illustrating the surface tension results for aqueous solutions including the surfactant Sodium Laurel Ether Sulfate and an experimental hydrophobically modified polymer at various concentrations and ratios between the surfactant and the hydrophobically modified polymer.

In FIG. 5, an experimental HMP (EXP. 3 from Table 2) was being tested in solution with the anionic surfactant A (sodium laurel ether sulfate—SLES—from Table 1) to determine how much of an increase in surface tension could be had for an aqueous solution including EXP. 3 and SLES in comparison to an aqueous solution including only SLES. The aqueous solution including the SLES surfactant and the EXP. 3 HMP had a concentration of combined surfactant and HMP of 0.01% and 0.05% and the aqueous solution that was used for comparative purposes and included only the SLES surfactant was prepared at the same concentration amounts. Ratios of surfactant:HMP tested in this experiment were 1:1, 2:1, and 5:1 and were tested at each concentration amount mentioned above. As depicted in FIG. 5, aqueous solutions including an HMP and a surfactant can increase the surface tension as compared to the surface tension for an aqueous solution including that surfactant alone. In some cases, the aqueous solutions including an HMP and a surfactant can increase the surface tension to above 45 mN/m.

Figure 6:
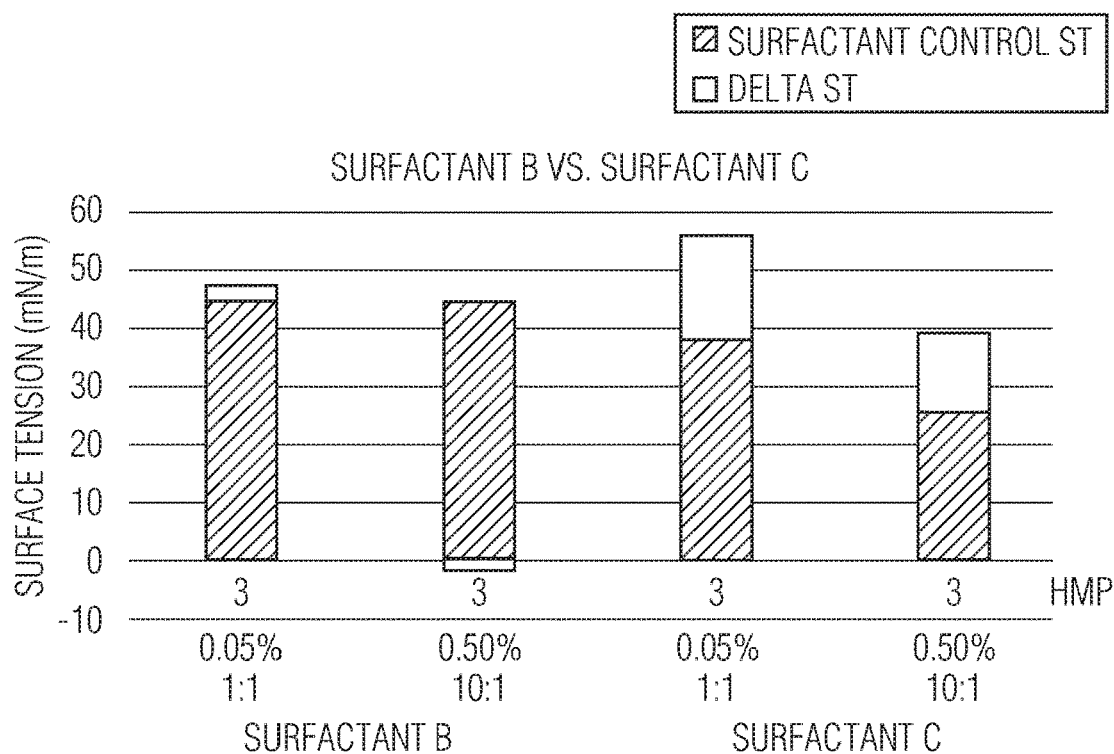
FIG. 6 is a graph illustrating the surface tension results for aqueous solutions including two respective surfactants (Laureth-23 and polyalkyleneoxidemethylsiloxane copolymer) and an experimental hydrophobically modified polymer at various concentrations and ratios between the surfactants and the hydrophobically modified polymer.

FIG. 6 shows a test that was conducted to screen two different surfactants against the same HMP. The HMP used in this testing was EXP. 3 from Table 2. The surfactants used in this testing were surfactants B and C from Table 1. Surfactant B is Laureth-23, a pure ethoxylate system which is representative of surfactant mixes that can be purchased by various vendors as most are ethoxylate based. Surfactant C is polyalkyleneoxidemethylsiloxane copolymer, a silicon based surfactant. The aqueous solutions including the surfactants and the HMPs had a concentration of combined surfactant and HMP of 0.05% and 0.50% and the aqueous solution that was used for comparative purposes and included only the SLES surfactant was prepared at the same concentration amounts. Ratios of surfactant:HMP tested in this experiment were 1:1 and 10:1 and were tested at each concentration amount mentioned above. As illustrated in FIG. 6, the aqueous solution including HMP EXP. 3 and surfactant B had either a small increase in surface tension compared to the comparative aqueous solution including only surfactant B, or had a decrease in surface tension compared to the comparative aqueous solution including only surfactant B. However, the aqueous solution including HMP EXP. 3 and surfactant C proved to increase surface tension over 10 mN/m in each test conducted. From this testing, it can be seen that some surfactant/HMP combinations in aqueous solution can aid in increasing surface tension, while others may have little noticeable increase, or even create a decrease in surface tension for an aqueous solution as compared to an aqueous solution including that respective surfactant alone. Thus, careful selection of the proper combination of an HMP and surfactant is required to provide the desired change in surface tension properties that one is looking to achieve.

Figure 7:
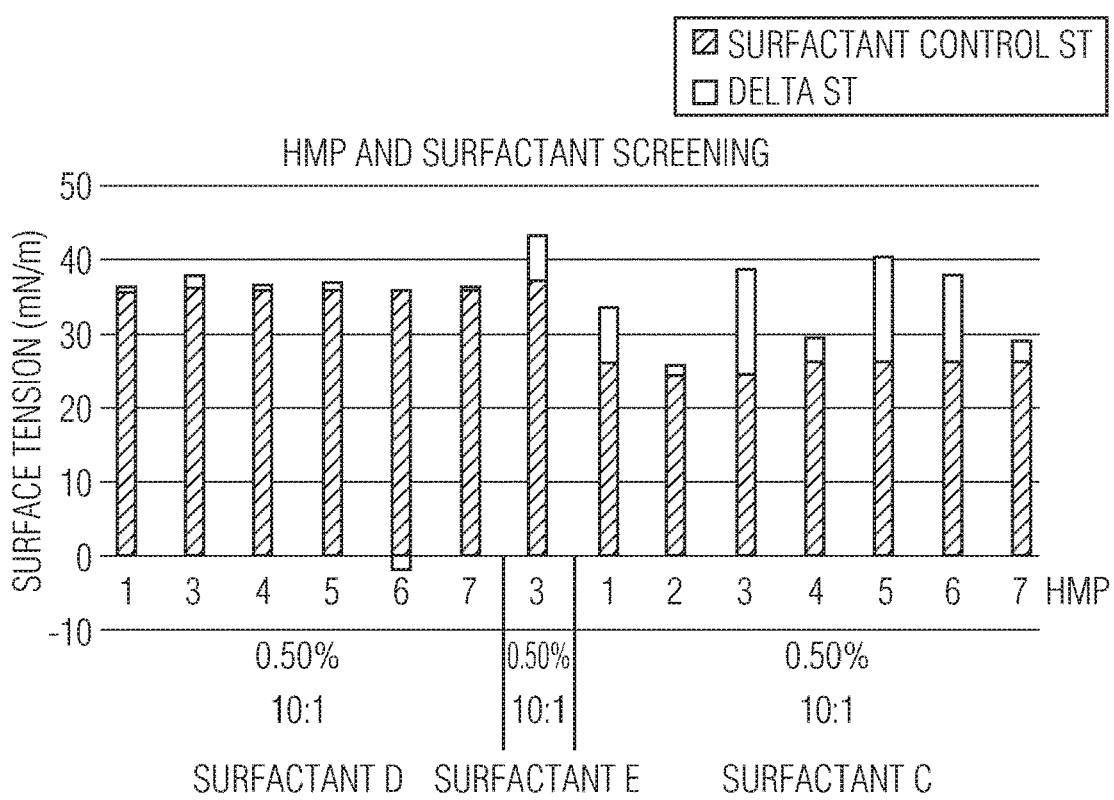
FIG. 7 is a graph illustrating the surface tension results for aqueous solutions including three respective surfactants (Sanoil 884, Silastol 163, and polyalkyleneoxidemethylsiloxane copolymer) and various hydrophobically modified polymers at various concentrations and ratios between the surfactants and the hydrophobically modified polymers.
Figure 8:
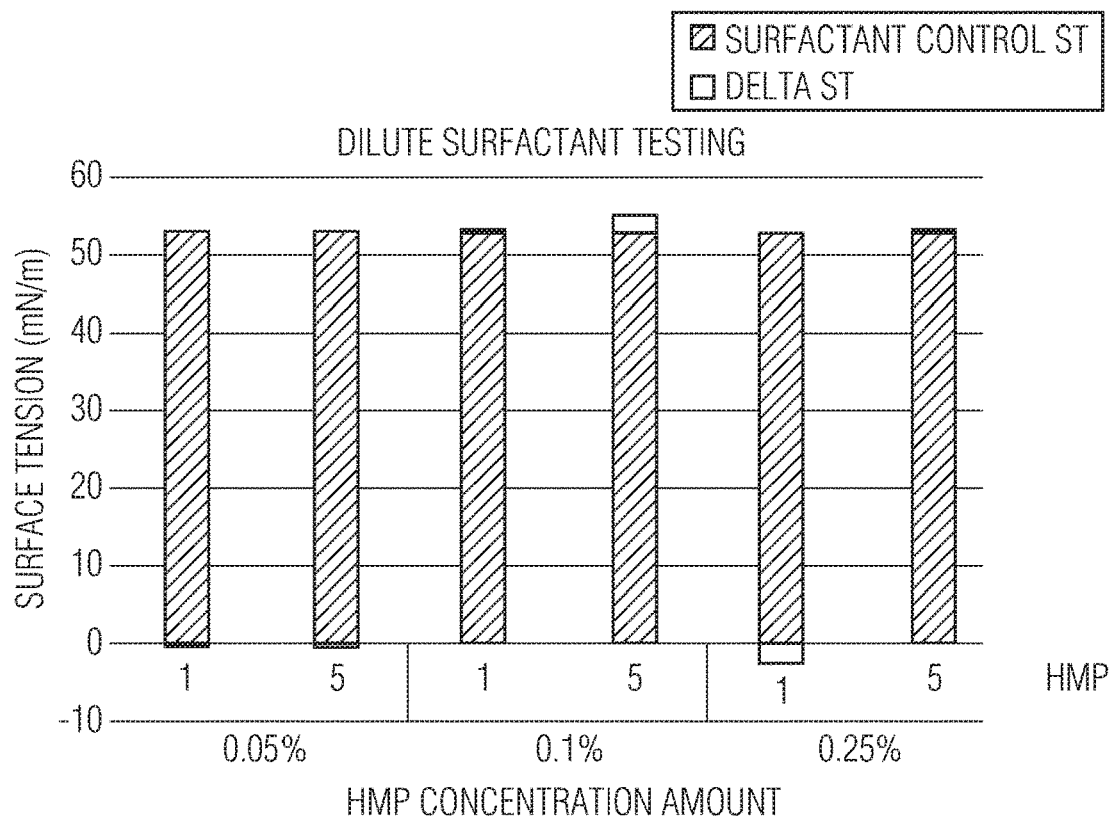
FIG. 8 is a graph illustrating the surface tension results for aqueous solutions including the surfactant polyalkyleneoxidemethylsiloxane copolymer and two different experimental hydrophobically modified polymers at a dilute ratio of surfactant:HMP of 1:10 and at various concentrations between the surfactant and the hydrophobically modified polymers.

Additional screening of various surfactant and HMP combinations is depicted in FIG. 7. Surfactants C, D, and E from Table 1 were tested with various HMPs from Table 2. As illustrated in FIG. 7, it was demonstrated that surfactant D provided was not suitable for increasing surface tension of an aqueous solution. However, surfactants C and E were successful at increasing surface tension with various HMPs, as depicted in FIG. 7. Specifically, HMPs 1, 3, 5, and 6 all demonstrated an ability to increase surface tension in conjunction with surfactant C, and HMP 3 demonstrated an ability to increase surface tension in conjunction with surfactant E. All testing conducted for FIG. 7 was completed such that the aqueous solutions had a concentration of 0.50% of combined surfactant and HMP (or only surfactant for comparative solution), and the ratio of surfactant:HMP in aqueous solutions was 10:1.

Additional testing was done to test how aqueous solutions would react to extremely dilute surfactant solutions used with HMPs. For this testing, surfactant C was tested in aqueous solution with HMP 1 and HMP 5 from Table 1, with the surfactant C concentration to HMP ratio being kept constant at a ratio of 1:10. The concentration of the HMPs from the aqueous solutions including surfactant C and an HMP was increased to be 0.05%, 0.10% and 0.25%, but keeping the surfactant:HMP ratio at 1:10. The concentration of the surfactant in the control solutions was adjusted to match the amount of the surfactant in the respective solutions including surfactant and HMP. From the testing results illustrated in FIG. 8, even at a 0.25% concentration of HMPs, surface tension could not be increased beyond approximately 54 mN/m. Based on this testing, it can be seen that the CAC for the respective HMP and surfactant combinations are being reached.

Figure 9:
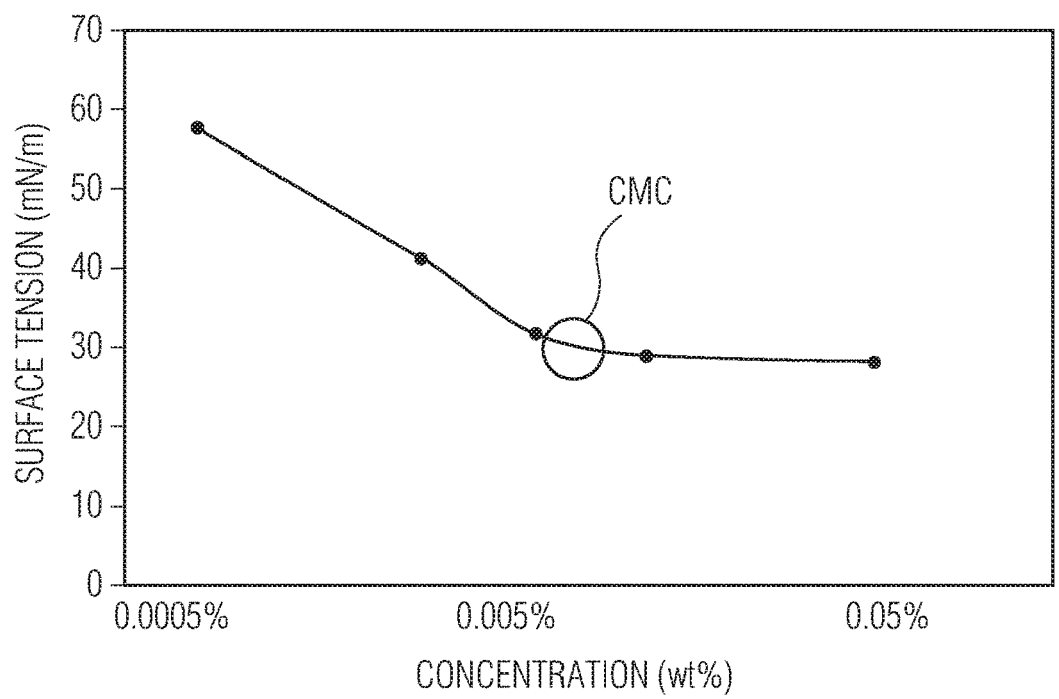
FIG. 9 is a graph illustrating a sample Critical Micelle Concentration (CMC) curve for an aqueous solution including a surfactant showing surface tension vs. concentration.

FIG. 9 illustrates a generic CMC curve for a surfactant that was used to be able to identify minute amounts of quenching by the HMPs. The surfactant was started at a concentration of 0.1% weight in solution. Further diluting the surfactant led to discovering where the plateau of the surface tension stopped and the surface tension began rising. As viewed in FIG. 9, the left-side of this plateau is considered the CMC, at approximately 0.006% surfactant for the surfactant tested in FIG. 9. Further testing of quenching for this surfactant with various HMPs was then conducted at this concentration of surfactant to allow for the most increase in surface tension to be realized. This testing was completed for surfactants F-V from Table 1. Once the CMC was discovered for all surfactants F-V, the equilibrium surface tension of the HMPs 8-14 in Table 2 at a 0.1% concentration in solution were taken alone to make sure that these HMPs did not reduce surface tension and behave as surfactants in their own regard.

Figure 10:
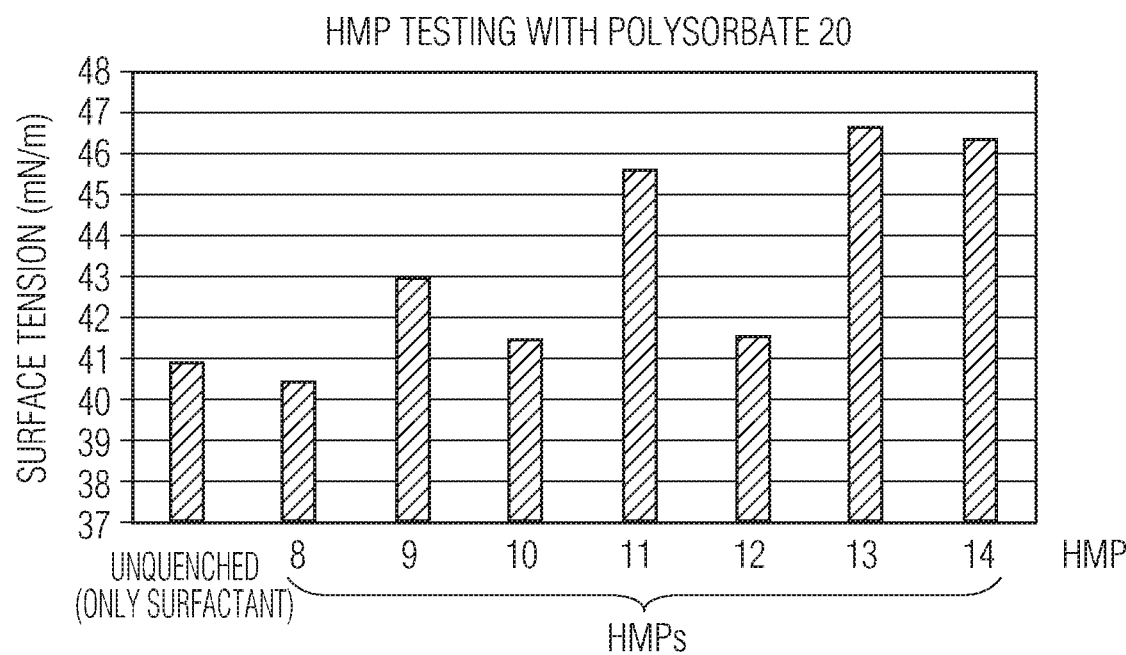
FIG. 10 is a graph illustrating the surface tension results for aqueous solutions including the surfactant polysorbate 20 and various hydrophobically modified polymers.

As illustrated in FIG. 10, several HMPs were then mixed with surfactant F (polysorbate 20) at a 1:1 ratio and surface tensions were compared to surface tensions for the aqueous solution including surfactant F alone ("unquenched"), which had a surface tension of approximately 41 mN/m. Several HMPs in the testing depicted in FIG. 10 demonstrated an ability to increase surface tension with surfactant F at least 2 mN/m as compared to the unquenched solution that only included surfactant F. This shows the ability of HMPs to quench surfactants by a significant amount. A significant change in surface tension was considered to be 2 mN/m or more from the pure surfactant solution. Any surfactant and HMP solution that showed this change was again tested at an HMP:surfactant ratio of 4:1 in order to show an upper limit of the capability of surfactant quenching.

FIGS. 11-15 depict results of additional Surface Tension Testing for HMPs from Table 2 in combination with various surfactants from Table 1. In each of the FIGS. 11-15, the surface tension is provided on the y-axis as the change in surface tension as compared to the respective control of the surface tension value for an aqueous solution including only the respective surfactant. The results of the Surface Tension Testing depicted in FIGS. 11-15 further demonstrate the unpredictability of combinations of surfactants and HMPs to combine to increase surface tension of an aqueous solution.

Figure 11:
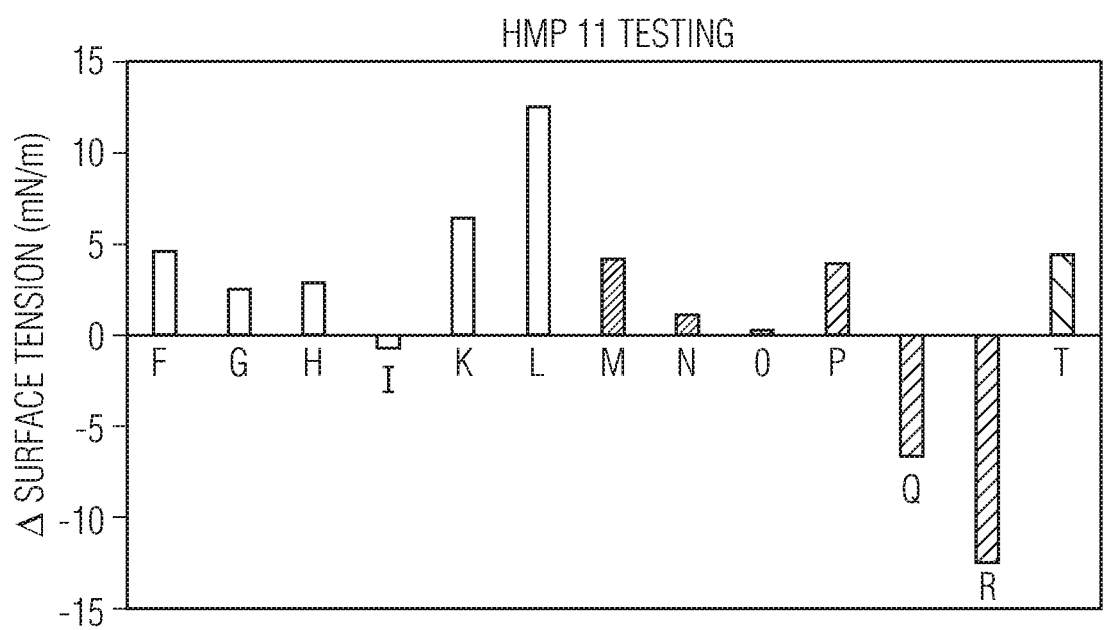
FIG. 11 is a graph illustrating the surface tension results for aqueous solutions including various surfactants and the hydrophobically modified polymer acrylates/vinyl neodecanoate crosspolymer.
Figure 12:
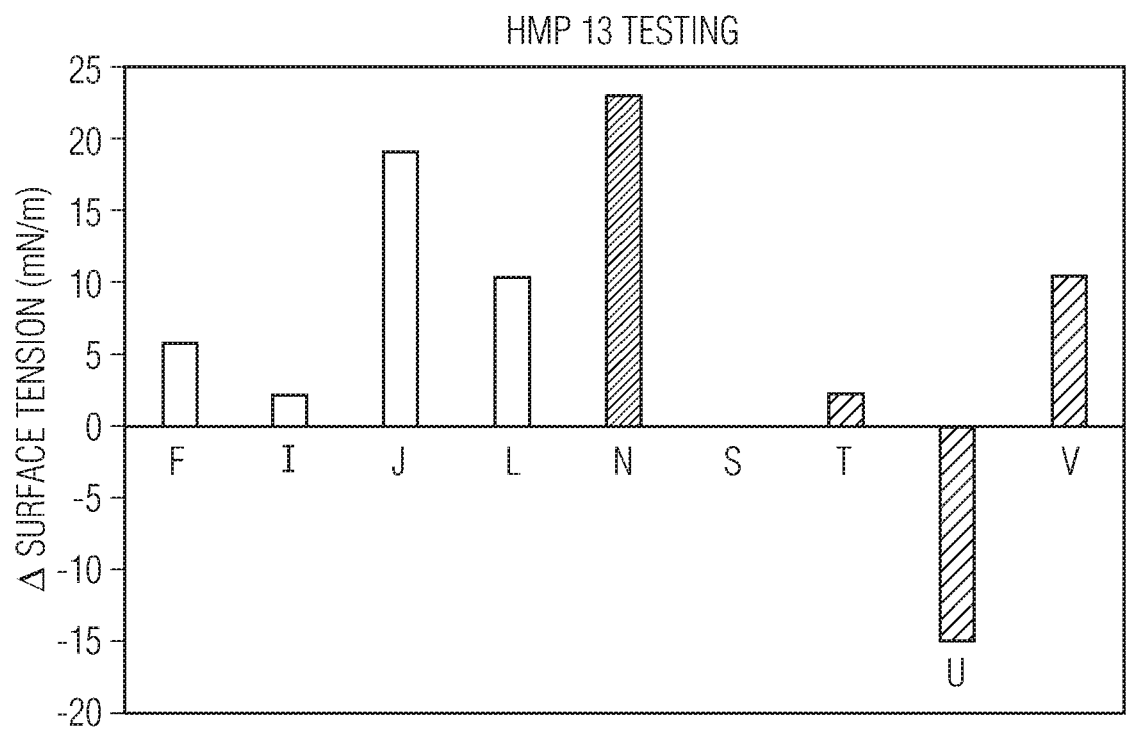
FIG. 12 is a graph illustrating the surface tension results for aqueous solutions including various surfactants and the hydrophobically modified polymer acrylates/beheneth-25 methacrylate copolymer.
Figure 13:
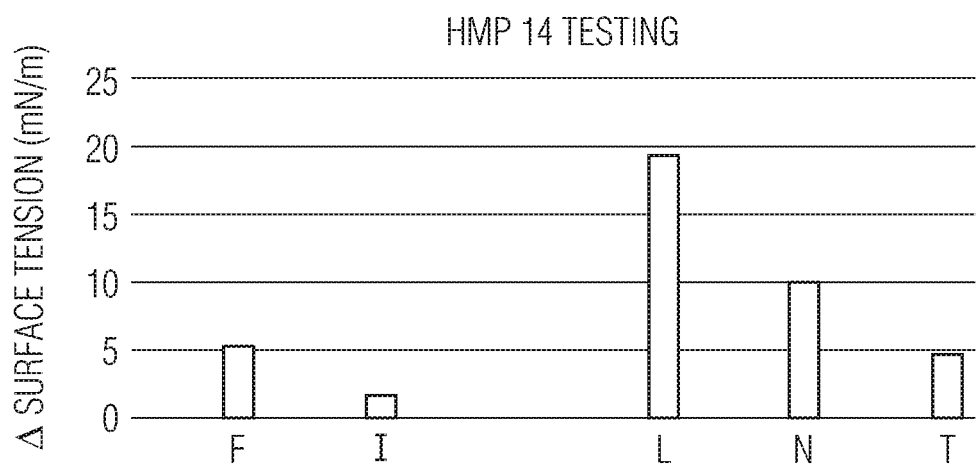
FIG. 13 is a graph illustrating the surface tension results for aqueous solutions including various surfactants and the hydrophobically modified polymer acrylates/steareth-20 methacrylate crosspolymer.

FIGS. 11-13 illustrate Surface Tension Testing results for acrylate based HMPs tested in an aqueous solution with various surfactants from Table 1. Specifically, FIG. 11 depicts the Surface Tension Testing results for HMP 11 (acrylates/vinyl neodecanoate crosspolymer), FIG. 12 depicts the Surface Tension Testing results for HMP 13 (acrylates/beheneth-25 methacrylate copolymer), and FIG. 13 depicts the Surface Tension Testing results for HMP 14 (acrylates/steareth-20 methacrylate crosspolymer). As illustrated in FIGS. 11-13, the acrylate based HMPs increased surface tension with several different surfactants, and saw the highest consistency to increase surface tension when combined with a nonionic surfactant, such as surfactants F, G, H, J, K, and L from Table 1. However, not all acrylate HMP and surfactant combinations increased surface tension in the test aqueous solutions. In fact, some combinations of the acrylate HMPs and surfactants even reduced surface tension.

Figure 14:
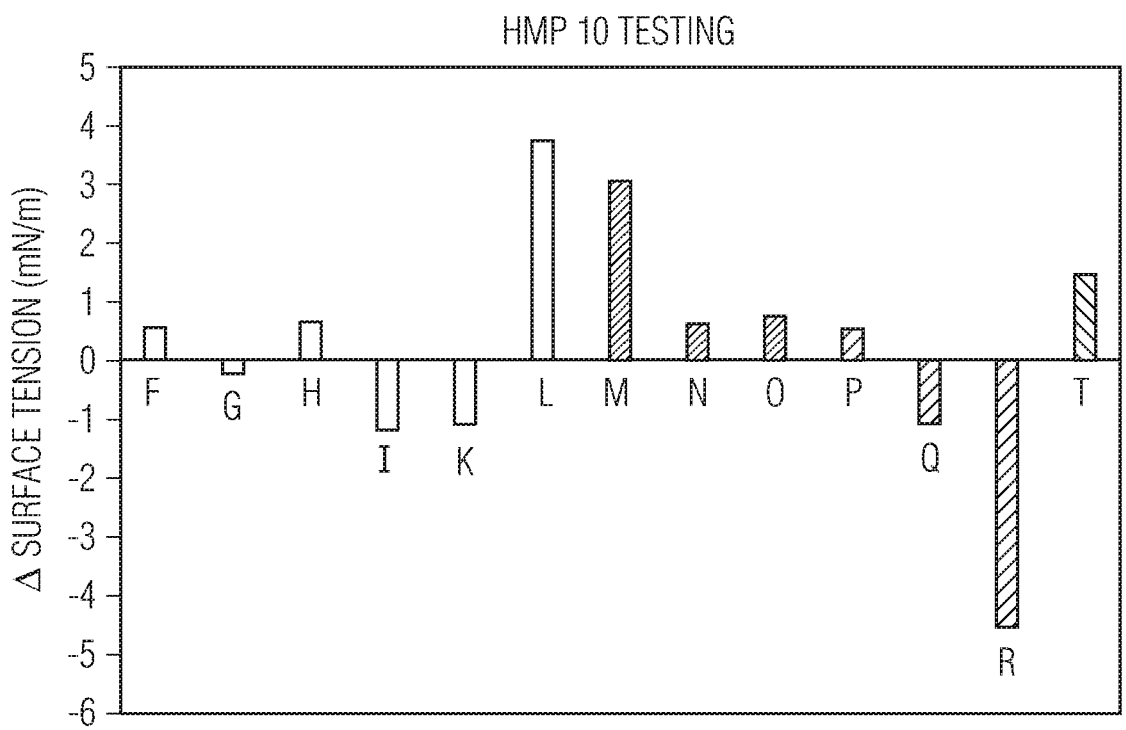
FIG. 14 is a graph illustrating the surface tension results for aqueous solutions including various surfactants and the hydrophobically modified polymer cetyl hydroxyethylcellulose.

FIG. 14 illustrates Surface Tension Testing results for a cellulosic based HMP (HMP 10 from Table 2) combined with various surfactants from Table 1. As illustrated in FIG. 14, the cellulosic based HMP 10 was successful at increasing surface tension at least 2 mN/m for an aqueous solution when combined with one nonionic surfactant (surfactant L) and one anionic surfactant (surfactant M). Other combinations of HMP 10 either produced less than a 2 mN/m increase in surface tension or reduced surface tension. Although not shown, cellulosic HMP polyvinylpyrrolidone (HMP 8 from Table 2) was not able to increase surface tension with any surfactant tested.

Figure 15:
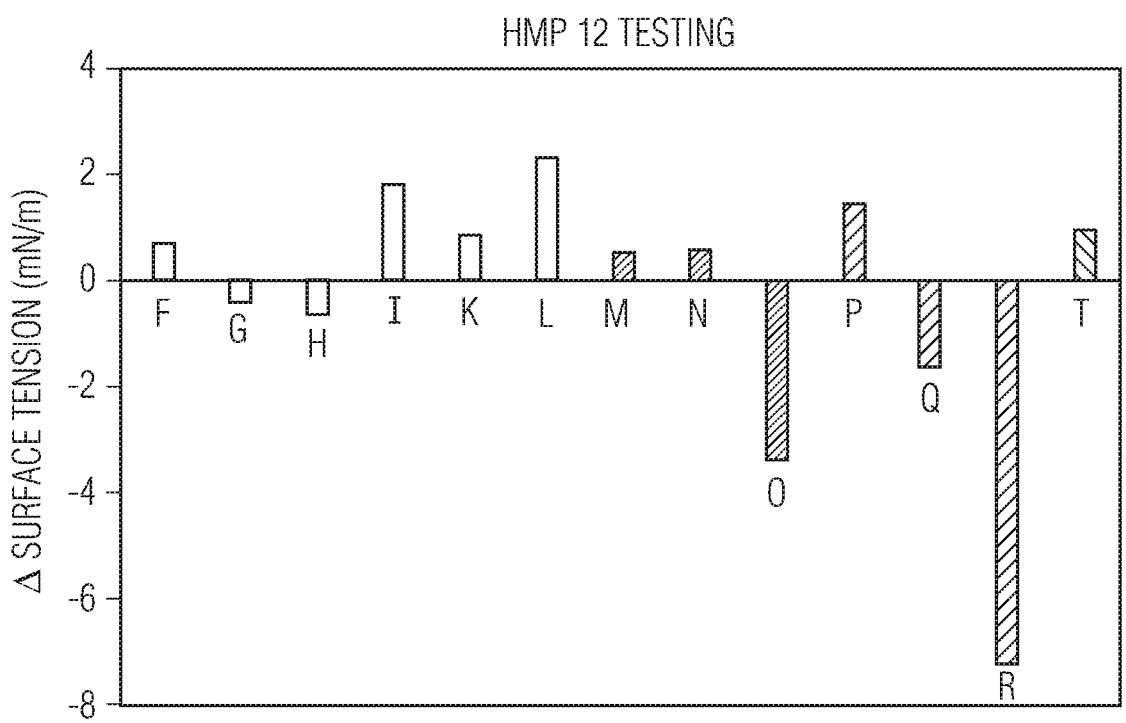
FIG. 15 is a graph illustrating the surface tension results for aqueous solutions including various surfactants and the hydrophobically modified polymer PEG-150/stearyl alcohol/SMDI copolymer.

FIG. 15 illustrates Surface Tension Testing results for a urethane based HMP (HMP 12 from Table 2) combined with various surfactants from Table 1. As illustrated in FIG. 15, the urethane based HMP 12 was successful at increasing surface tension at least 2 mN/m for an aqueous solution when combined with two nonionic surfactants (surfactants I and L). However, other combinations of HMP 12 either produced less than a 2 mN/m increase in surface tension or reduced surface tension.

Figure 16:
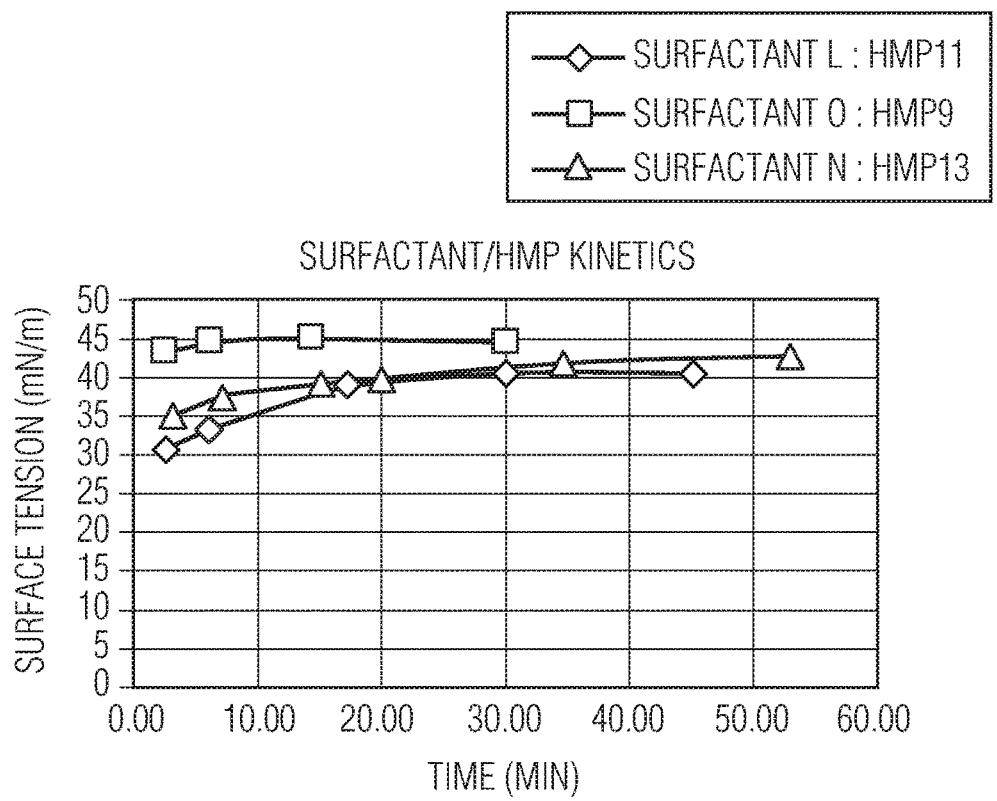
FIG. 16 is graph illustrating the surface tension results of three aqueous solutions including three different surfactant/hydrophobically modified polymer combinations over time.

Testing was also conducted to determine the kinetics of the surface tension properties of the HMP and surfactant aqueous solution over time. FIG. 16 illustrates three different combinations of HMP and surfactant solutions, which were chosen due to their strong ability to increase surface tension as compared to the particular comparative surfactant solution. Importantly, the HMP and the surfactant combinations are not quenched immediately. In other words, the HMP and the surfactant aqueous solutions increased in surface tension over time, and can take as long as 30 minutes or more to be fully quenched.

Because the HMP and surfactants do not quench immediately when placed into an aqueous solution, the HMP and the surfactant may each be applied to the same component of the absorbent article 10 or absorbent assembly 44 without negatively affecting intake properties. For example, the bodyside liner 28 could be treated with both an HMP and a surfactant, and because the surface tension properties may not increase immediately after the HMP and surfactant are put into an aqueous solution but take several minutes, the HMP and surfactant will not negatively impact the intake properties of the bodyside liner 28 and the purpose for treating the bodyside liner 28 with the surfactant to reduce surface tension in the first place. However, once the HMP and surfactant quench over time (i.e., once the surface tension of the aqueous solution increases), the potential of re-wet or leakage of the aqueous solution from the absorbent assembly 44 and/or absorbent article 10 decreases.

Figure 17:
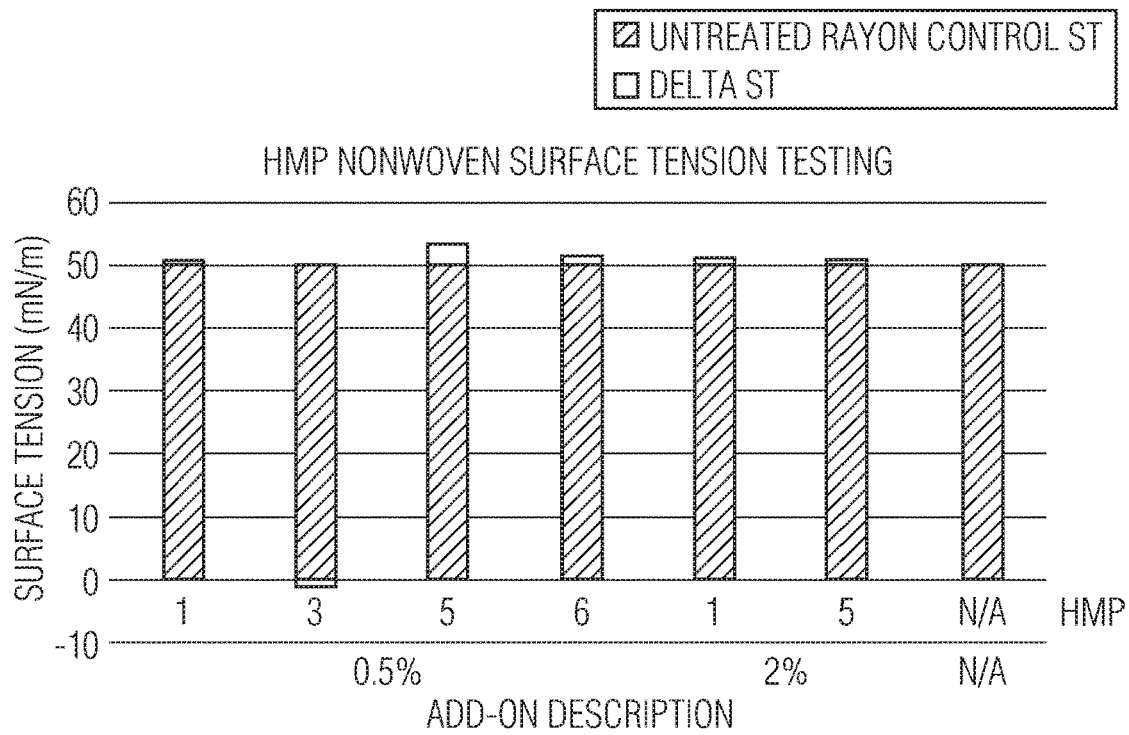
FIG. 17 is a graph illustrating the surface tension results of for aqueous solutions including the surfactant polyalkyleneoxidemethylsiloxane copolymer and various hydrophobically modified polymers at various add-on percentages from a rayon substrate.

Fluid transfer layer 46 treatment with HMPs was tested to simulate product performance with various materials. Polypropylene based fluid transfer layers 46 are naturally hydrophobic, and thus, treating a polypropylene based fluid transfer layer 46 affected intake through such a material. However, hydrophilic materials may also be used as a fluid transfer layer 46. One exemplary hydrophilic material that may compose the fluid transfer layer 46 is rayon. A rayon fluid transfer layer 46 was treated with various HMPs, as shown below in FIG. 17, without negatively affecting fluid intake. This testing involved using an add-on of 0.5% of surfactant C from Table 1 to a sample acquisition layer 48 (hollow polypropylene (HPP) BCW) and a sample bodyside liner 28 (polypropylene (PP) SMS). Surface Tension testing results with such a system having various HMPs applied to the rayon fluid transfer layer 46 at add-on levels of 0.5% and 2.0% are shown in FIG. 17. The far right bar in FIG. 17 provides a control system surface tension, which was an untreated rayon fluid transfer layer 46 with the 0.5% surfactant C treatment to the bodyside liner 28 and acquisition layer 48. The change in surface tension from the control system to each tested HMP system showed that only HMP 5 provided above a 2 mN/m increase in surface tension, providing an increase of approximately 4 mN/m. The testing showed that all of the surface tension tests on nonwovens with HMPs, no matter add-on percent, stayed around 52 mN/m, showing that the surfactant:HMP ratio of 1:4 provided that the CAC had been reached.

As shown from the testing described herein, an absorbent assembly 44 and/or an absorbent article 10 can include at least one component treated with a surfactant (such as a bodyside liner 28) to help with intake properties and can also include at least one component treated with an HMP that is configured to interact with the surfactant upon the absorbent assembly 44 and/or the absorbent article 10 being wetted such that when the surfactant and the HMP are in an aqueous solution, the surface tension of the aqueous solution increases. As noted above, the HMP could be used to treat any component of the absorbent assembly 44 and/or the absorbent article 10 that will come in contact with the aqueous solution upon an insult of body exudates. Preferably, the component treated with the HMP is at least one of: the bodyside liner 28, the acquisition layer 48, the fluid transfer layer 46, and the absorbent body 34. By having an increased surface tension, the aqueous solution is less likely to flow-back towards the wearer's skin and/or leak from the absorbent article.

Test Methods

Surface Tension Test Method

Figure 18:
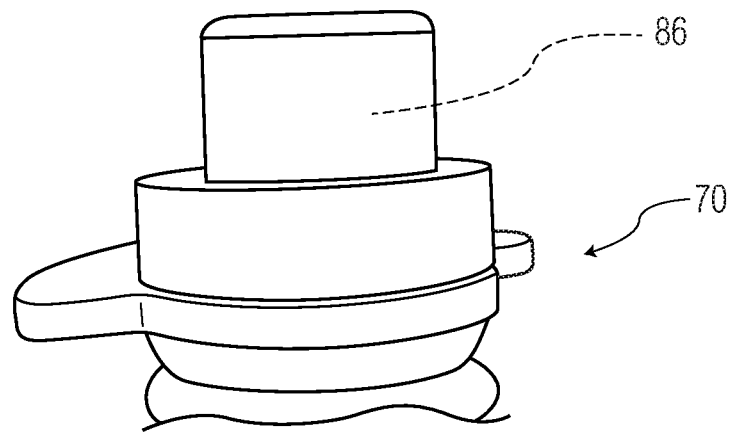
FIG. 18 illustrates a Wilhelmy plate tensiometer serving as part of the equipment for the Surface Tension Test Method as described herein.
Figure 19:
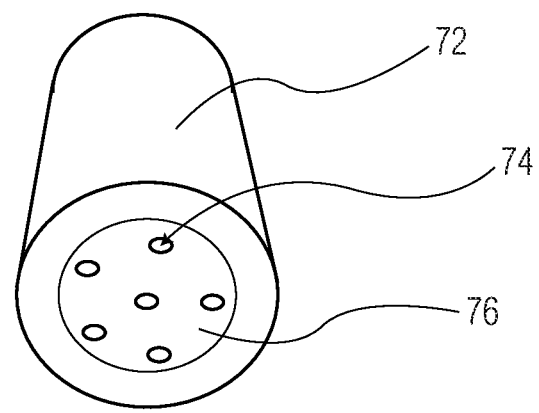
FIG. 19 illustrates a container with apertures serving as part of the equipment for the Surface Tension Test Method as described herein.
Figure 20:
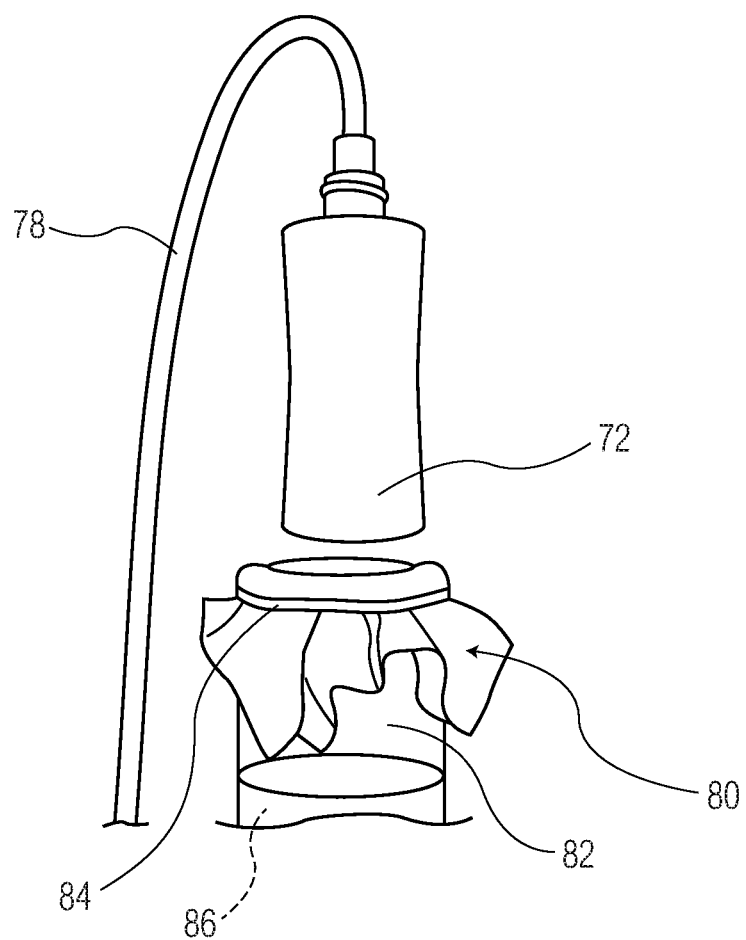
FIG. 20 illustrates the equipment of FIGS. 18 and 19 for the set-up of the Surface Tension Test Method as described herein.

The Surface Tension Test Method tested for the equilibrium surface tension of an aqueous solution. The equipment used for this test method are illustrated in FIGS. 18-20. FIG. 18 illustrates a Wilhelmy Plate Tensiometer 70. To more accurately simulate an insult, a 9 oz. plastic cylindrical container 72 having a diameter of approximately four centimeters had six apertures 74 (only one aperture 74 labeled in FIG. 19 for purposes of clarity) drilled in to the bottom surface 76, as shown in FIG. 19. The apertures 74 were approximately 1 mm in diameter and were spaced according to the depiction in FIG. 19, with one aperture 74 being in the center of the bottom surface 76 of the container 72 and the other five apertures 74 spaced approximately equidistant from one another in a circular fashion about the central aperture 74. This pattern of apertures 74 was configured to more accurately simulate the larger wetting pattern on an absorbent assembly 44 observed in actual use, as opposed to a single stream insult from a pump. As illustrated in FIG. 20, the cylindrical container 72 was attached to a pump (not shown) through a flexible tubing 78 and positioned on a stand approximately 12.7 mm (½ inch) from the top of a nonwoven layers sample 80. The nonwoven layers sample 80 was wrapped over an opening in a collection basin 82 and secured in place with a rubber band 84, as illustrated in FIG. 20, such that the nonwoven layers sample 80 was taut over the opening in the collection basin 82.

The nonwoven layers sample 80 was modified for each particular surfactant/HMP combination that were testing for the surface tension of an aqueous solution including the surfactant and HMP and comparative samples that were testing for surface tension of aqueous solutions including only a surfactant. Describing from bottom-most layer and moving upwards towards the cylindrical container 72, the nonwoven layers sample 80 includes a layer of 40 gsm rayon to simulate a fluid transfer layer 46, a layer of 80 gsm HPP BCW nonwoven material treated with the surfactant at the specified concentration and amount to simulate an acquisition layer 48, and a layer of 12 gsm SMS material treated with surfactant at the specified concentration and amount to simulate the bodyside liner 28. In testing codes involving the HMPs, the layer of rayon material was treated with the specified HMP at the specified concentration and amount. In control runs, the layer of rayon was not treated.

A pump (not shown) in the testing equipment was set to insult 85 mL of a saline solution at 15 mL/s. The insult of 85 mL passed through the flexible tubing 78 and into the cylindrical container 72, dispersed through the six apertures 74 in the bottom surface 76 of the container 72, onto the nonwoven layers sample 80 being tested and into the collection basin 82 where it was captured. As soon as the insult was complete, the collection basin 82 was removed, the nonwoven layers sample 80 was discarded, and the aqueous solution 86 in the collection basin 82 was taken to the Wilhelmy Plate Tensiometer to test the equilibrium surface tension of the aqueous solution 86 (as illustrated in FIG. 18). Three repetitions of each test was completed.

Embodiments

Embodiment 1: An absorbent article, comprising: a bodyside liner, the bodyside liner being treated with a surfactant; an outer cover; an absorbent body, the absorbent body being disposed between the bodyside liner and the outer cover; and wherein a component of the absorbent article is treated with a hydrophobically modified polymer, the hydrophobically modified polymer being configured to interact with the surfactant upon wetting of the absorbent article when the surfactant and the hydrophobically modified polymer are in an aqueous solution to increase surface tension of the aqueous solution.

Embodiment 2: The absorbent article of embodiment 1, wherein the hydrophobically modified polymer and the surfactant interact to increase a surface tension of a test solution at least 2 mN/m as measured by the Surface Tension Test Method as described herein.

Embodiment 3: The absorbent article of embodiment 1 or embodiment 2, wherein the hydrophobically modified polymer is an acrylate hydrophobically modified polymer.

Embodiment 4: The absorbent article of embodiment 3, wherein the acrylate hydrophobically modified polymer is selected from the group consisting of: acrylates/vinyl neodecanoate crosspolymer, acrylates/beheneth-25 methacrylate copolymer, and acrylates/steareth-20 methacrylate crosspolymer.

Embodiment 5: The absorbent article of any of the preceding embodiments, wherein the surfactant is non-ionic.

Embodiment 6: The absorbent article of claim 5, wherein the surfactant comprises at least one of polysorbate 20, cocamide DIPA, decyl glucoside, PEG-7 glyceryl cocoate, PEG-6 caprylic/capric glycerides, and perfluorononylethyl carboxydecyl PEG-10 dimethicone.

Embodiment 7: The absorbent article of any one of embodiments 1-4, wherein the surfactant is anionic.

Embodiment 8: The absorbent article of embodiment 7, wherein the surfactant comprises at least one of sodium laurylglucosides hydroxypropylsulfonate, cetyl phosphate, and caprylyl/capryl glucoside.

Embodiment 9: The absorbent article of any one of embodiments 1-4, wherein the surfactant is zwitterionic.

Embodiment 10: The absorbent article of claim 9, wherein the surfactant is sodium bis-hydroxyethylglycinate laurylglucosides crosspolymer and cocamidopropyl betaine.

Embodiment 11: The absorbent article of embodiment 3, wherein the hydrophobically modified polymer is acrylates/vinyl neodecanoate crosspolymer and the surfactant comprises at least one of polysorbate 20, cocamide DIPA, PEG-7 glyceryl cocoate, PEG-6 caprylic/capric glycerides, perfluorononylethyl carboxydecyl PEG-10 dimethicone, sodium laurylglucosides hydroxypropylsulfonate, cetyl phosphate, cetyltrimethylammonium bromide, and sodium bis-hydroxyethylglycinate lauryl-glucosides crosspolymer.

Embodiment 12: The absorbent article of embodiment 3, wherein the hydrophobically modified polymer is acrylates/beheneth-25 methacrylate copolymer and the surfactant comprises at least one of polysorbate 20, decyl glucoside, caprylyl/capryl gluocoside, perfluorononylethyl carboxydecyl PEG-10 dimethicone, cetyl phosphate, sodium bis-hydroxyethylglycinate lauryl-glucosides crosspolymer, and cocamidopropyl betaine.

Embodiment 13: The absorbent article of embodiment 3, wherein the hydrophobically modified polymer is acrylates/steareth-20 methacrylate crosspolymer and the surfactant comprises at least one of polysorbate 20, perfluorononylethyl carboxydecyl PEG-10 dimethicone, cetyl phosphate, sodium bis-hydroxyethylglycinate lauryl-glucosides crosspolymer, and caprylyl/capryl glucoside.

Embodiment 14: The absorbent article of embodiment 1 or embodiment 2, wherein the hydrophobically modified polymer is a cellulosic hydrophobically modified polymer.

Embodiment 15: The absorbent article of embodiment 14, wherein the hydrophobically modified polymer is hydroxylethylcellulose and the surfactant comprises at least one of perfluorononylethyl carboxydecyl PEG-10 dimethicone, and sodium laurylglucosides hydroxypropylsulfonate.

Embodiment 16: The absorbent article of embodiment 1 or embodiment 2, wherein the hydrophobically modified polymer is a urethane hydrophobically modified polymer.

Embodiment 17: The absorbent article of embodiment 16, wherein the hydrophobically modified polymer is PEG-150/stearyl alcohol/SMDI copolymer and the surfactant comprises at least one of decyl glucoside and perfluorononylethyl carboxydecyl PEG-10 dimethicone.

Embodiment 18: The absorbent article of any one of embodiments 1-4, wherein the surfactant is a silicon based surfactant.

Embodiment 19: The absorbent article of embodiment 18, wherein the surfactant is polyalkyleneoxidemethylsiloxane copolymer and the hydrophobically modified polymer comprises at least one of VP/acrylates/lauryl methacrylate copolymer and polyquaternium-55.

Embodiment 20: The absorbent article of any one of the preceding embodiments, further comprising a fluid transfer layer, the fluid transfer layer at least partially enveloping the absorbent body.

Embodiment 21: The absorbent article of embodiment 20, wherein the fluid transfer layer is hydrophilic, and wherein the fluid transfer layer is the component of the absorbent article treated with the hydrophobically modified polymer.

Embodiment 22: The absorbent article of any one of the preceding embodiments, wherein the hydrophobically modified polymer is disposed on a surface of the absorbent body.

Embodiment 23: The absorbent article of any one of the preceding embodiments, further comprising an acquisition layer, the acquisition layer being disposed between the bodyside liner and the absorbent body, wherein acquisition layer is the component of the absorbent article treated with the hydrophobically modified polymer.

Embodiment 24: The absorbent article of any one of the preceding embodiments, wherein the bodyside liner is the component of the absorbent article treated with the hydrophobically modified polymer.

Embodiment 25: The absorbent article of any one of the preceding embodiments, wherein a ratio of the surfactant to the acrylate hydrophobically modified polymer is between about 1:1 to about 10:1.

Embodiment 26: An absorbent assembly for use in an absorbent article that includes a surfactant for reducing surface tension of an aqueous solution, the absorbent assembly comprising: an absorbent body comprising absorbent material; a component of the absorbent assembly being treated with a hydrophobically modified polymer, the hydrophobically modified polymer configured to interact with the surfactant upon wetting of the absorbent assembly when the surfactant and the hydrophobically modified polymer are in an aqueous solution to increase surface tension of the aqueous solution.

Embodiment 27: The absorbent assembly of embodiment 26, further comprising a bodyside liner.

Embodiment 28: The absorbent assembly of embodiment 27, further comprising the surfactant, wherein the bodyside liner is the treated with the surfactant.

Embodiment 29: The absorbent assembly of embodiment 28, further comprising an outer cover, wherein the absorbent body is disposed between the bodyside liner and the outer cover.

Embodiment 30: The absorbent assembly of any one of embodiments 26-29, further comprising a fluid transfer layer, the fluid transfer layer at least partially enveloping the absorbent body.

Embodiment 31: The absorbent assembly of embodiment 30, wherein the fluid transfer layer is hydrophilic, and wherein the fluid transfer layer is the component of the absorbent assembly treated with the hydrophobically modified polymer.

Embodiment 32: The absorbent assembly of any one of embodiments 26-30, wherein the absorbent body is the component of the absorbent assembly that is treated with the hydrophobically modified polymer.

Embodiment 33: The absorbent assembly of any one of embodiments 26-32, wherein the hydrophobically modified polymer is an acrylate hydrophobically modified polymer.

Embodiment 34: The absorbent assembly of embodiment 33, wherein the acrylate hydrophobically modified polymer is selected from the group consisting of: acrylates/vinyl neodecanoate crosspolymer, acrylates/beheneth-25 methacrylate copolymer, and acrylates/steareth-20 methacrylate crosspolymer.

All documents cited in the Detailed Description are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by references, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
a bodyside liner, the bodyside liner being treated with a surfactant;
an outer cover;
an absorbent body, the absorbent body being disposed between the bodyside liner and the outer cover; and
wherein a component of the absorbent article is treated with a hydrophobically modified polymer, the hydrophobically modified polymer being configured to interact with the surfactant upon wetting of the absorbent article when the surfactant and the hydrophobically modified polymer are in an aqueous solution to increase surface tension of the aqueous solution in comparison to an aqueous solution including only the surfactant, wherein the hydrophobically modified polymer is an acrylate hydrophobically modified polymer.

2. The absorbent article of claim 1, wherein the hydrophobically modified polymer and the surfactant interact to increase a surface tension of a test solution at least 2 mN/m as measured by the Surface Tension Test Method.

3. The absorbent article of claim 1, wherein the acrylate hydrophobically modified polymer is selected from the group consisting of: acrylates/vinyl neodecanoate crosspolymer, acrylates/beheneth-25 methacrylate copolymer, and acrylates/steareth-20 methacrylate crosspolymer.

4. The absorbent article of claim 1, wherein the surfactant is non-ionic.

5. The absorbent article of claim 4, wherein the surfactant comprises at least one of polysorbate 20, cocamide DIPA, decyl glucoside, PEG-7 glyceryl cocoate, PEG-6 caprylic/capric glycerides, and perfluorononylethyl carboxydecyl PEG-10 dimethicone.

6. The absorbent article of claim 1, wherein the surfactant is anionic.

7. The absorbent article of claim 6, wherein the surfactant comprises at least one of sodium laurylglucosides hydroxypropylsulfonate, cetyl phosphate, and caprylyl/capryl glucoside.

8. The absorbent article of claim 1, wherein the surfactant is zwitterionic.

9. The absorbent article of claim 8, wherein the surfactant is sodium bis-hydroxyethylglycinate lauryl-glucosides crosspolymer and cocamidopropyl betaine.

10. The absorbent article of claim 1, wherein the hydrophobically modified polymer is acrylates/vinyl neodecanoate crosspolymer and the surfactant comprises at least one of polysorbate 20, cocamide DIPA, PEG-7 glyceryl cocoate, PEG-6 caprylic/capric glycerides, perfluorononylethyl carboxydecyl PEG-10 dimethicone, sodium laurylglucosides hydroxypropylsulfonate, cetyl phosphate, cetryltrimethylammonium bromide, and sodium bis-hydroxyethylglycinate lauryl-glucosides crosspolymer.

11. The absorbent article of claim 1, wherein the hydrophobically modified polymer is acrylates/beheneth-25 methacrylate copolymer and the surfactant comprises at least one of polysorbate 20, decyl glucoside, caprylyl/capryl gluocoside, perfluorononylethyl carboxydecyl PEG-10 dimethicone, cetyl phosphate, sodium bis-hydroxyethylglycinate lauryl-glucosides crosspolymer, and cocamidopropyl betaine.

12. The absorbent article of claim 1, wherein the hydrophobically modified polymer is acrylates/steareth-20 methacrylate crosspolymer and the surfactant comprises at least one of polysorbate 20, perfluorononylethyl carboxydecyl PEG-10 dimethicone, cetyl phosphate, sodium bis-hydroxyethylglycinate lauryl-glucosides crosspolymer, and caprylyl/capryl glucoside.

13. The absorbent article of claim 1, wherein the surfactant is a silicon based surfactant.

14. The absorbent article of claim 13, wherein the surfactant is polyalkyleneoxidemethylsiloxane copolymer and the hydrophobically modified polymer comprises at least one of VP/acrylates/lauryl methacrylate copolymer and polyquaternium-55.

15. The absorbent article of claim 1, further comprising a fluid transfer layer, the fluid transfer layer at least partially enveloping the absorbent body.

16. The absorbent article of claim 15, wherein the fluid transfer layer is hydrophilic, and wherein the fluid transfer layer is the component of the absorbent article treated with the hydrophobically modified polymer.

17. The absorbent article of claim 1, wherein the hydrophobically modified polymer is disposed on a surface of the absorbent body.

18. The absorbent article of claim 1, further comprising an acquisition layer, the acquisition layer being disposed between the bodyside liner and the absorbent body, wherein acquisition layer is the component of the absorbent article treated with the hydrophobically modified polymer.

19. The absorbent article of claim 1, wherein a ratio of the surfactant to the hydrophobically modified polymer is between about 1:1 to about 10:1.

* * * * *